US008821799B2

(12) United States Patent
Bassler et al.

(10) Patent No.: US 8,821,799 B2
(45) Date of Patent: Sep. 2, 2014

(54) METHOD AND SYSTEM IMPLEMENTING SPATIALLY MODULATED EXCITATION OR EMISSION FOR PARTICLE CHARACTERIZATION WITH ENHANCED SENSITIVITY

(75) Inventors: Michael Bassler, Menlo Park, CA (US); Peter Kiesel, Palo Alto, CA (US); Oliver Schmidt, Palo Alto, CA (US); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 614 days.

(21) Appl. No.: 11/698,409

(22) Filed: Jan. 26, 2007

(65) Prior Publication Data

US 2008/0181827 A1    Jul. 31, 2008

(51) Int. Cl.
*G01N 33/00*  (2006.01)
*G01N 21/75*  (2006.01)
*C12Q 1/68*  (2006.01)

(52) U.S. Cl.
USPC .................... 422/105; 422/82.01; 422/82.05; 422/119; 435/6.1; 436/172

(58) Field of Classification Search
None
See application file for complete search history.

(56) References Cited

U.S. PATENT DOCUMENTS

| | | | |
|---|---|---|---|
| 2,708,389 A | 5/1955 | Kavanagh | |
| 3,357,230 A | 12/1967 | Topaz | |
| 3,797,911 A | 3/1974 | Kogelnik et al. | |
| 3,915,573 A | 10/1975 | Knoll et al. | |
| 3,958,252 A | 5/1976 | Kashio | |
| 3,973,118 A | 8/1976 | LaMontagne | |
| 4,081,277 A | 3/1978 | Brault et al. | |
| 4,131,899 A | 12/1978 | Christou | |
| 4,251,733 A * | 2/1981 | Hirleman, Jr. | ................. 250/575 |
| 4,427,296 A | 1/1984 | Demarest et al. | |
| 4,455,089 A | 6/1984 | Yeung et al. | |

(Continued)

FOREIGN PATENT DOCUMENTS

| | | |
|---|---|---|
| EP | 0354067 | 2/1990 |
| EP | 0442738 | 8/1991 |

(Continued)

OTHER PUBLICATIONS

Adams et al "Microfluidic integration on detector arrays for absorption and fluoescence micro-spectrometers" Sensors and Actuators, 2003, 104:25-31.*

(Continued)

*Primary Examiner* — Betty Forman
(74) *Attorney, Agent, or Firm* — Hollingsworth Davis, LLC

(57) ABSTRACT

A method and system for using spatially modulated excitation/emission and relative movement between a particle (cell, molecule, aerosol, ... ) and an excitation/emission pattern are provided. In at least one form, an interference pattern of the excitation light with submicron periodicity perpendicular to the particle flow is used. As the particle moves along the pattern, emission is modulated according to the speed of the particle and the periodicity of the stripe pattern. A single detector, which records the emission over a couple of stripes, can be used. The signal is recorded with a fast detector readout in order to capture the "blinking" of the particles while they are moving through the excitation pattern. This concept enables light detection with high signal-to-noise ratio and high spatial resolution without the need of expensive and bulky optics.

28 Claims, 21 Drawing Sheets

(56) References Cited

U.S. PATENT DOCUMENTS

| | | | |
|---|---|---|---|
| 4,514,257 A | 4/1985 | Karlsson et al. | |
| 4,536,762 A | 8/1985 | Moates | |
| 4,573,796 A | 3/1986 | Martin et al. | |
| 4,715,672 A | 12/1987 | Duguay et al. | |
| 4,730,922 A | 3/1988 | Bach et al. | |
| 4,764,670 A | 8/1988 | Pace et al. | |
| 4,793,705 A * | 12/1988 | Shera | 356/318 |
| 4,820,042 A | 4/1989 | Barger | |
| 4,822,998 A | 4/1989 | Yokota et al. | |
| 4,957,371 A | 9/1990 | Pellicori et al. | |
| 4,959,674 A | 9/1990 | Khuri-Yakub et al. | |
| 4,976,542 A | 12/1990 | Smith | |
| 5,028,545 A | 7/1991 | Soini | |
| 5,080,462 A | 1/1992 | Goto | |
| 5,144,498 A | 9/1992 | Vincent | |
| 5,151,585 A | 9/1992 | Siebert | |
| 5,159,199 A | 10/1992 | Labaw | |
| 5,166,755 A | 11/1992 | Gat | |
| 5,218,426 A | 6/1993 | Hall et al. | |
| 5,243,614 A | 9/1993 | Wakata et al. | |
| 5,254,919 A | 10/1993 | Bridges et al. | |
| 5,281,305 A | 1/1994 | Lee et al. | |
| 5,305,082 A | 4/1994 | Bret | |
| 5,312,535 A | 5/1994 | Waska et al. | |
| 5,324,401 A | 6/1994 | Yeung et al. | |
| 5,370,842 A | 12/1994 | Miyazaki et al. | |
| 5,394,244 A | 2/1995 | Tsai | |
| 5,410,404 A | 4/1995 | Kersey et al. | |
| 5,414,508 A | 5/1995 | Takahashi et al. | |
| 5,434,667 A * | 7/1995 | Hutchins et al. | 356/338 |
| 5,437,840 A | 8/1995 | King et al. | |
| 5,445,934 A | 8/1995 | Fodor et al. | |
| 5,491,347 A | 2/1996 | Allen et al. | |
| 5,528,045 A | 6/1996 | Hoffman et al. | |
| 5,572,328 A | 11/1996 | Fouckhardt et al. | |
| 5,608,517 A | 3/1997 | Munk | |
| 5,631,734 A | 5/1997 | Stern et al. | |
| 5,666,195 A | 9/1997 | Shultz et al. | |
| 5,674,698 A * | 10/1997 | Zarling et al. | 435/7.92 |
| 5,677,769 A | 10/1997 | Bendett | |
| 5,682,038 A | 10/1997 | Hoffman | |
| 5,745,308 A | 4/1998 | Spangenberg | |
| 5,760,900 A | 6/1998 | Ito et al. | |
| 5,777,329 A | 7/1998 | Westphal et al. | |
| 5,784,507 A | 7/1998 | Holm-Kennedy et al. | |
| 5,792,663 A | 8/1998 | Fry et al. | |
| 5,793,485 A | 8/1998 | Gourley | |
| 5,798,222 A | 8/1998 | Goix | |
| 5,801,831 A | 9/1998 | Sargoytchev | |
| 5,825,792 A | 10/1998 | Villeneuve et al. | |
| 5,864,641 A | 1/1999 | Murphy et al. | |
| 5,872,655 A | 2/1999 | Seddon et al. | |
| 5,876,674 A | 3/1999 | Dosoretz et al. | |
| 5,880,474 A | 3/1999 | Norton et al. | |
| 5,909,278 A * | 6/1999 | Deka et al. | 356/318 |
| 5,917,606 A | 6/1999 | Kaltenbach | |
| 5,933,233 A | 8/1999 | Gunther | |
| 5,945,676 A | 8/1999 | Khalil et al. | |
| 5,953,138 A | 9/1999 | Ellis | |
| 5,958,122 A | 9/1999 | Fukuda et al. | |
| 5,982,478 A | 11/1999 | Ainsworth et al. | |
| 5,982,534 A | 11/1999 | Pinkel et al. | |
| 6,040,578 A | 3/2000 | Malin et al. | |
| 6,049,727 A | 4/2000 | Crothall | |
| 6,066,243 A | 5/2000 | Anderson et al. | |
| 6,091,502 A | 7/2000 | Weigl et al. | |
| 6,108,463 A | 8/2000 | Herron et al. | |
| 6,116,718 A | 9/2000 | Peeters et al. | |
| 6,122,536 A | 9/2000 | Sun et al. | |
| 6,137,117 A | 10/2000 | Feldstein et al. | |
| 6,169,604 B1 | 1/2001 | Cao | |
| 6,187,592 B1 | 2/2001 | Gourley | |
| 6,192,168 B1 | 2/2001 | Feldstein et al. | |
| 6,216,022 B1 | 4/2001 | Tyrrell et al. | |
| 6,249,346 B1 | 6/2001 | Chen et al. | |
| 6,275,628 B1 | 8/2001 | Jones et al. | |
| 6,285,504 B1 | 9/2001 | Diemeer | |
| 6,295,130 B1 | 9/2001 | Sun et al. | |
| 6,306,933 B1 | 10/2001 | Eiger et al. | |
| 6,307,623 B1 | 10/2001 | Papuchon et al. | |
| 6,310,690 B1 | 10/2001 | Cao et al. | |
| 6,353,475 B1 | 3/2002 | Jensen et al. | |
| 6,399,405 B1 | 6/2002 | Chen et al. | |
| 6,405,073 B1 | 6/2002 | Crowley et al. | |
| 6,429,022 B1 | 8/2002 | Kunz et al. | |
| 6,438,397 B1 | 8/2002 | Bosquet et al. | |
| 6,459,080 B1 | 10/2002 | Yin et al. | |
| 6,468,702 B1 | 10/2002 | Yi et al. | |
| 6,483,959 B1 | 11/2002 | Singh et al. | |
| 6,490,034 B1 | 12/2002 | Woias et al. | |
| 6,505,775 B1 | 1/2003 | Gu et al. | |
| 6,514,460 B1 | 2/2003 | Fendrock | |
| 6,519,037 B2 | 2/2003 | Jung et al. | |
| 6,525,308 B1 | 2/2003 | Schmidt-Hattenberger | |
| 6,558,945 B1 | 5/2003 | Kao | |
| 6,577,780 B2 | 6/2003 | Lockhart | |
| 6,580,507 B2 | 6/2003 | Fry et al. | |
| 6,603,548 B2 | 8/2003 | Church et al. | |
| 6,608,679 B1 | 8/2003 | Chen et al. | |
| 6,628,390 B1 | 9/2003 | Johnson | |
| 6,630,999 B2 | 10/2003 | Shroder | |
| 6,639,679 B2 | 10/2003 | Frojdh | |
| 6,665,113 B2 | 12/2003 | Aso et al. | |
| 6,678,502 B1 | 1/2004 | Sugaya | |
| 6,694,158 B2 | 2/2004 | Polak | |
| 6,697,542 B2 | 2/2004 | Platzman et al. | |
| 6,700,664 B1 | 3/2004 | Honda et al. | |
| 6,704,104 B2 | 3/2004 | Li | |
| 6,710,871 B1 | 3/2004 | Goix | |
| 6,736,484 B2 | 5/2004 | Nakamura | |
| 6,742,884 B2 | 6/2004 | Wong et al. | |
| 6,747,285 B2 | 6/2004 | Schueller et al. | |
| 6,755,983 B2 | 6/2004 | Yudasaka | |
| 6,759,713 B2 | 7/2004 | Chabinyc et al. | |
| 6,768,555 B2 | 7/2004 | Chen et al. | |
| 6,781,690 B2 | 8/2004 | Armstrong et al. | |
| 6,785,002 B2 | 8/2004 | Zarrabian et al. | |
| 6,795,190 B1 | 9/2004 | Paul et al. | |
| 6,796,710 B2 | 9/2004 | Yates et al. | |
| 6,800,849 B2 | 10/2004 | Staats | |
| 6,806,925 B2 | 10/2004 | Ishii et al. | |
| 6,809,865 B2 | 10/2004 | Chen | |
| 6,815,125 B1 | 11/2004 | Okabe et al. | |
| 6,816,257 B2 | 11/2004 | Goix | |
| 6,830,856 B2 | 12/2004 | Tsai et al. | |
| 6,838,361 B2 | 1/2005 | Takeo | |
| 6,839,140 B1 | 1/2005 | O'Keefe et al. | |
| 6,856,718 B2 | 2/2005 | Kane et al. | |
| 6,865,198 B2 | 3/2005 | Taubman et al. | |
| 6,867,420 B2 | 3/2005 | Mathies et al. | |
| 6,867,868 B1 | 3/2005 | Barbarossa | |
| 6,870,149 B2 | 3/2005 | Berezin | |
| 6,872,320 B2 | 3/2005 | Wong et al. | |
| 6,872,588 B2 | 3/2005 | Chabinyc et al. | |
| 6,887,713 B2 | 5/2005 | Nelson et al. | |
| 6,890,050 B2 | 5/2005 | Ready et al. | |
| 6,906,792 B2 | 6/2005 | Ortyn et al. | |
| 6,927,852 B2 | 8/2005 | Reel | |
| 6,934,435 B2 | 8/2005 | Kane | |
| 6,952,603 B2 | 10/2005 | Gerber et al. | |
| 6,972,261 B2 | 12/2005 | Wong et al. | |
| 6,983,176 B2 | 1/2006 | Gardner et al. | |
| 7,011,630 B2 | 3/2006 | Desai et al. | |
| 7,024,236 B2 | 4/2006 | Ford et al. | |
| 7,034,933 B2 | 4/2006 | Walker et al. | |
| 7,046,357 B2 | 5/2006 | Weinberger et al. | |
| 7,064,836 B2 | 6/2006 | Bechtel et al. | |
| 7,106,441 B2 | 9/2006 | Sun et al. | |
| 7,130,321 B2 | 10/2006 | Spinelli et al. | |
| 7,136,161 B2 | 11/2006 | Nakamura | |
| 7,149,396 B2 | 12/2006 | Schmidt et al. | |
| 7,195,465 B2 | 3/2007 | Kane et al. | |
| 7,195,797 B2 | 3/2007 | Mearini et al. | |
| 7,248,361 B2 | 7/2007 | Kiesel et al. | |

(56) References Cited

U.S. PATENT DOCUMENTS

| | | | |
|---|---|---|---|
| 7,252,360 B2 | 8/2007 | Hersch et al. | |
| 7,259,856 B2 | 8/2007 | Kachanov et al. | |
| 7,268,868 B2 | 9/2007 | Kiesel et al. | |
| 7,274,011 B2 | 9/2007 | Tennant et al. | |
| 7,277,569 B2 | 10/2007 | Bruce et al. | |
| 7,291,824 B2 | 11/2007 | Kiesel et al. | |
| 7,298,478 B2 | 11/2007 | Gilbert et al. | |
| 7,305,112 B2 | 12/2007 | Curry et al. | |
| 7,310,153 B2 | 12/2007 | Kiesel et al. | |
| 7,315,667 B2 | 1/2008 | Schmidt et al. | |
| 7,355,699 B2 | 4/2008 | Gilbert et al. | |
| 7,358,476 B2* | 4/2008 | Kiesel et al. | 250/208.2 |
| 7,365,022 B2 | 4/2008 | Wong et al. | |
| 7,372,435 B2 | 5/2008 | Kim | |
| 7,386,199 B2 | 6/2008 | Schmidt et al. | |
| 7,387,892 B2 | 6/2008 | Kiesel et al. | |
| 7,391,517 B2 | 6/2008 | Trebbia et al. | |
| 7,420,677 B2 | 9/2008 | Schmidt et al. | |
| 7,433,552 B2 | 10/2008 | Kiesel et al. | |
| 7,440,101 B2 | 10/2008 | Auer et al. | |
| 7,456,953 B2 | 11/2008 | Schmidt et al. | |
| 7,466,307 B2 | 12/2008 | Trent, Jr. | |
| 7,466,409 B2 | 12/2008 | Scherer et al. | |
| 7,471,399 B2 | 12/2008 | Kiesel et al. | |
| 7,479,625 B2 | 1/2009 | Kiesel et al. | |
| 7,496,463 B2 | 2/2009 | Nicoli et al. | |
| 7,502,123 B2 | 3/2009 | Kiesel et al. | |
| 7,506,268 B2 | 3/2009 | Jennings | |
| 7,521,769 B2 | 4/2009 | Cunningham | |
| 7,522,786 B2 | 4/2009 | Kiesel et al. | |
| 7,529,438 B2 | 5/2009 | Schmidt et al. | |
| 7,545,513 B2 | 6/2009 | Kiesel et al. | |
| 7,547,904 B2 | 6/2009 | Schmidt et al. | |
| 7,554,673 B2* | 6/2009 | Kiesel et al. | 356/519 |
| 7,633,629 B2 | 12/2009 | Kiesel et al. | |
| 7,641,777 B2 | 1/2010 | Joseph et al. | |
| 7,694,231 B2 | 4/2010 | Kocienda | |
| 7,701,580 B2 | 4/2010 | Bassler et al. | |
| 7,718,948 B2 | 5/2010 | Kiesel | |
| 7,763,856 B2* | 7/2010 | Kiesel et al. | 250/343 |
| 7,817,254 B2 | 10/2010 | Hegyi et al. | |
| 7,817,276 B2 | 10/2010 | Kiesel et al. | |
| 7,830,517 B2 | 11/2010 | Beck et al. | |
| 7,839,450 B2 | 11/2010 | Hing | |
| 7,879,390 B2 | 2/2011 | Saileo et al. | |
| 8,223,127 B2 | 7/2012 | Park | |
| 2002/0155485 A1 | 10/2002 | Kao | |
| 2003/0000835 A1 | 1/2003 | Witt et al. | |
| 2003/0020915 A1 | 1/2003 | Schueller et al. | |
| 2003/0077660 A1 | 4/2003 | Pien et al. | |
| 2003/0137672 A1 | 7/2003 | Moriya et al. | |
| 2003/0161024 A1 | 8/2003 | Zhang et al. | |
| 2003/0169311 A1 | 9/2003 | Kong Leong et al. | |
| 2003/0178555 A1 | 9/2003 | Fang | |
| 2003/0189711 A1 | 10/2003 | Orr et al. | |
| 2003/0191377 A1 | 10/2003 | Robinson et al. | |
| 2003/0197754 A1 | 10/2003 | Nakamura | |
| 2003/0231272 A1 | 12/2003 | Nakamura et al. | |
| 2003/0235924 A1 | 12/2003 | Adams et al. | |
| 2004/0031684 A1 | 2/2004 | Witt | |
| 2004/0038386 A1 | 2/2004 | Zesch et al. | |
| 2004/0057050 A1* | 3/2004 | Beck et al. | 356/336 |
| 2004/0067167 A1* | 4/2004 | Zhang et al. | 422/82.05 |
| 2004/0109659 A1 | 6/2004 | Aylward et al. | |
| 2004/0110099 A1 | 6/2004 | Kozawa et al. | |
| 2004/0132214 A1 | 7/2004 | Lin et al. | |
| 2004/0141884 A1 | 7/2004 | Unno et al. | |
| 2004/0175734 A1 | 9/2004 | Stahler et al. | |
| 2004/0178523 A1 | 9/2004 | Kim et al. | |
| 2004/0223881 A1 | 11/2004 | Cunningham et al. | |
| 2004/0228375 A1 | 11/2004 | Ghosh et al. | |
| 2004/0253835 A1 | 12/2004 | Kawase | |
| 2005/0042615 A1 | 2/2005 | Smith et al. | |
| 2005/0046821 A1* | 3/2005 | Hanson et al. | 356/3.01 |
| 2005/0068526 A1 | 3/2005 | Arrutshy | |
| 2005/0099624 A1 | 5/2005 | Staehr et al. | |
| 2005/0128479 A1 | 6/2005 | Gilbert et al. | |
| 2005/0136358 A1 | 6/2005 | Paul et al. | |
| 2005/0162650 A1 | 7/2005 | Yamamoto | |
| 2005/0164320 A1 | 7/2005 | McDevitt et al. | |
| 2005/0213082 A1 | 9/2005 | DiBernardo et al. | |
| 2005/0255392 A1 | 11/2005 | Tsai et al. | |
| 2006/0115749 A1 | 6/2006 | Toyoda | |
| 2006/0121555 A1 | 6/2006 | Lean | |
| 2006/0182659 A1 | 8/2006 | Unlu et al. | |
| 2006/0193550 A1 | 8/2006 | Wawro et al. | |
| 2006/0203224 A1 | 9/2006 | Sebastian et al. | |
| 2006/0268260 A1 | 11/2006 | Liu et al. | |
| 2007/0009380 A1 | 1/2007 | Cunningham | |
| 2007/0046301 A1 | 3/2007 | Kasapi | |
| 2007/0076210 A1 | 4/2007 | Kiesel et al. | |
| 2007/0116609 A1 | 5/2007 | Baeuerle et al. | |
| 2007/0145249 A1 | 6/2007 | Kiesel et al. | |
| 2007/0165225 A1* | 7/2007 | Trainer | 356/335 |
| 2007/0166725 A1 | 7/2007 | McBride et al. | |
| 2007/0186791 A1 | 8/2007 | Kim et al. | |
| 2007/0201025 A1 | 8/2007 | Greenwald | |
| 2008/0013092 A1 | 1/2008 | Maltezos et al. | |
| 2008/0095985 A1 | 4/2008 | Frey et al. | |
| 2008/0181827 A1* | 7/2008 | Bassler et al. | 422/119 |
| 2008/0183418 A1 | 7/2008 | Bassler et al. | |
| 2008/0186483 A1 | 8/2008 | Kiesel et al. | |
| 2008/0186494 A1 | 8/2008 | Kiesel et al. | |
| 2008/0186504 A1 | 8/2008 | Kiesel et al. | |
| 2008/0186508 A1 | 8/2008 | Kiesel et al. | |
| 2008/0187011 A1 | 8/2008 | Kiesel et al. | |
| 2009/0016690 A1 | 1/2009 | Schmidt et al. | |
| 2009/0195852 A1 | 8/2009 | Bassler et al. | |
| 2009/0220189 A1 | 9/2009 | Kiesel et al. | |
| 2010/0155572 A1 | 6/2010 | Kiesel et al. | |
| 2010/0155577 A1 | 6/2010 | Kiesel et al. | |
| 2010/0157291 A1 | 6/2010 | Kiesel et al. | |
| 2010/0201988 A1 | 8/2010 | Kiesel | |
| 2010/0261288 A1 | 10/2010 | Recknor et al. | |
| 2011/0222062 A1 | 9/2011 | Martini et al. | |
| 2013/0037726 A1 | 2/2013 | Kiesel et al. | |
| 2013/0037728 A1 | 2/2013 | Kiesel et al. | |

FOREIGN PATENT DOCUMENTS

| | | |
|---|---|---|
| EP | 1324018 | 7/2003 |
| EP | 1653217 | 5/2006 |
| EP | 1800752 | 6/2007 |
| EP | 1801553 | 6/2007 |
| EP | 1801562 | 6/2007 |
| EP | 1801564 | 6/2007 |
| EP | 1950552 | 7/2008 |
| JP | 02049143 | 2/1990 |
| JP | 02245638 | 10/1990 |
| JP | 03020642 | 1/1991 |
| JP | 04223261 | 8/1992 |
| JP | 04297888 | 10/1992 |
| JP | 06018421 | 1/1994 |
| JP | 2004252214 | 9/2004 |
| JP | 2005165073 | 6/2005 |
| JP | 2007518991 | 6/2007 |
| WO | WO9520144 | 7/1995 |
| WO | WO9944042 | 9/1999 |
| WO | WO9954730 | 10/1999 |
| WO | WO0039573 | 7/2000 |
| WO | WO0062050 | 10/2000 |
| WO | WO02/25269 | 3/2002 |
| WO | 2004033059 | 4/2004 |
| WO | WO2004063681 | 7/2004 |
| WO | WO2004/083820 | 9/2004 |
| WO | WO2005017498 | 2/2005 |
| WO | WO2005/108963 | 11/2005 |
| WO | WO2006/133360 | 12/2006 |
| WO | WO2007069840 | 6/2007 |

OTHER PUBLICATIONS

European Search Report dated Oct. 18, 2010 issued in EP08150482.1.

(56) References Cited

OTHER PUBLICATIONS

"4-Channel Optical Transceiver Applying 3-Dimensional Polymeric Waveguide", FIND, vol. 24, No. 4, 2006, pp. 1-5.
Adams et al., "Microfluidic Integration on Detector Arrays for Absorption and Fluorescence Micro-spectrometer", Sensors and Actuators, 2003, pp. 25-31.
Agilent Technologies, "Agilent 83453B High-Resolution Spectrometer—Technical Specifications", Feb. 2005, pp. 1-8.
Agilent Technologies "Developing Technology: HPLC-Chip/MS", May 25, 2011, 2 pages.
Bassler et al., "Class Identification of Bio-Molecules Based on Multicolor Native Fluorescence Spectroscopy", Optics, East 2006, Session SA201, 2006. (abstract only).
Becker et al., "Polymer Microfabrication Methods for Microfluidic Analytical Applications", Electrophoresis, vol. 21, 2000, pp. 12-26. (abstract only).
Bernini et al., "Silicon Micromachined Hollow Optical Waveguides for Sensing applications", IEEE Journal on Selected Topics in Quantum Electronics, vol. 8, No. 1, Jan./Feb. 2002, pp. 106-110. (abstract only).
Bese et al., "A compact, affordable and portable CD4 T-cell machine", Int. Conf. AIDS 2002, Jul. 7-12, 2002, 1 pg. (no copy available).
Bhatta et al., "Rapid Identification of Microorganisms by Intrinsic Fluorescence", Proc. of SPIE, vol. 5699, 2005, pp. 9-18.
Bracewell, R.N., The Fourier Transform and Its Applications, $2^{nd}$ Ed., McGraw-Hill, 1978, Table of Contents and pp. 24-50, 98-126, and 177-188. (No copy available).
Cheung et al., "Impedance Spectroscopy Flow Cytometry: On-Chip Label-Free Cell Differentiation", Cytometry Part A, vol. 65A, 2005, pp. 124-132.
Cunningham et al., "Label-Free Assays on the Bind System", Journal of Biomolecular Screening, vol. 9, No. 6, 2004, pp. 481-490.
Devasenathipathy et al., "3 Electrokinetic Flow Diagnostics", in Breuer K.S. Ed. Micro-and Nano-Scale Diagnostic Techniques, Springer Verlag, New York, 2003, pp. 121-166.
"Flow Cytometry", printed from www.wellscenter.iupui.edu/MMIA on Jan. 29, 2008, 4 pages. (no copy available).
Fuhr, Measuring with Light, Sensors Magazine Online, May 2000, 11 pages.
Fuji-Keizai USA, "Biosensor Market, R&D and Commercial Implication", 2004, 5 pages.
Henry et al., "Wavelength Response of Thin-Film Optical Position-Sensitive Detectors", J. Opt. A: Pure Appl. Opt., vol. 4, 2002, pp. 527-534. (abstract only).
Hoffman, R. A., "Flow Cytometry: Instrumentation, Applications, Future Trends and Limitations", Springer Series on Fluorescence, vol. 6, 2008, pp. 307-342. (no copy available).
Holmes et al., "Label-Free Differential Leukocyte Counts Using a Microfabricated, Single-Cell Impedance Spectrometer", Sensors, 2007 IEEE, pp. 1452-1455. (abstract only).
Imade et al., "Comparison of a New, Affordable Flow Cytometric Method and the Manual Magnetic Bead Technique for CD4 T-Lymphocyte Counting in a Northern Nigerian Setting", Clinical and Diagnostic Laboratory Imm., Jan. 2005, p. 224-227. (no copy available).
Janossy et al., "Affordable CD4+-T-Cell Counting by Flow Cytometry:CD45 gating for Volumetric Analysis", Clinical and Diagnostic Laboratory Immunology, Sep. 2002, p. 1085-1094. (no copy available).
Johnson et al., "Introductions to Photonic Crystals: Bloch's Theorem, Band Diagrams, and Gaps (But No Defects)", Feb. 3, 2003, 16 pages.
Johnson, "Photonic Crystals: Periodic Surprises in Electromagnetism", printed from ab-initio.mit.edu on Oct. 5, 2006, 29 pages.
Jones et al., "Dielectrophoretic Liquid Actuation Nanodroplet Formation", Journal of Applied Physics, vol. 89, No. 2, 2001, pp. 1441-1448. (abstract only).
Kalvaram et al., "Precision moulding techniques for optical waveguide devices", SPIE, vol. 3135, 1997, pp. 2-11. (abstract only).

Kiesel et al., "Hand-held flow cytometer for point of care CD4 testing", APS March Meeting 2010, vol. 55, No. 2, 3 pages. (no copy available).
Kiesel et al., "Spatially Modulated Emission Advances Point-of-Care Diagnostics", Laser Focus World, Nov. 2010, pp. 47-50.
Kiesel et al., "Spatially modulated fluorescence emission from moving particles", Applied Physics Letters, vol. 94, 2009, 3 pages.
Konsziela, "Accurately Measure Laser Spectral Characteristics", 2006, 5 pages.
Kim et al., "Polymer-Planar-Lightwave-Circuit-Type Variable Optical Attenuator Fabricated by Hot Embossing Process" ETRI Journal, vol. 27, No. 1, Feb. 2004, pp. 122-125.
Law et al., "Low-Voltage Superlattice Asymmetric Fabry-Perot Reflection Modulator", IEEE Phot. Tech. Lett, vol. 3, No. 4, Apr. 1991, pp. 324-326. (abstract only).
Liang et al., "Refractive Index Measurement of Single Living Cell Using a Biophotonic Chip for Cancer Diagnosis Applications", $9^{th}$ International Conference on Miniaturized Systems for Chemistry and Life Sciences, Oct. 2005, pp. 464-466.
Liu et al., "Nanowell Surface Enhanced Raman Scattering Arrays Fabricated by Soft-Lithography for Label-Free Biomolecular Detections in Integrated Microfluidics", Applied Physics Letters, vol. 87, 2005, pp. 1-3.
McNichols et al., "Optical Glucose Sensing in Biological Fluids: An Overview", Journal of Biomedical Optics, vol. 5, No. 1, Jan. 2000, pp. 5-16. (abstract only).
"Optical Chopper—SR540—Optical Chopper System", Stanford Research Systems, Oct. 2008, 2 pages. (no copy available).
Othonos et al. "Fiber-Bragg Gratings—Fundamentals and Applications in Telecommunications and Sensing", Artech House, Norwood, MA, 1999, pp. 304-330 (no copy available).
Prassad, "Introduction to Biophotonics", John Wiley & Sons, Hoboken, N.J. 2003, pp. 311-356. (no copy available).
Schaefer et al., "Accuracy of Position Detection Using a Position-Sensitive Detector", IEEE Transactions on Instrumentation and Measurement, vol. 47, No. 4, Aug. 1998, pp. 914-919. (abstract only).
Schmidt et al., "Guiding Light in Fluids", applied Physics Letters, vol. 88, 2006, pp. 151109-1-1151109-14.
Schmidt et al., "Enhanced light-target interaction using a novel anti-resonant waveguide concept", SPIE Proc. 6094, 2006, pp. 80-89.
Schmidt et al., "Fluorescence Spectrometer-on-a-fluidic-chip", Lab Chop, 2007. (abstract only).
Shapiro, H.M., Practical Flow Cytometry, Fourth Edition, Wiley-Liss, 2003, Table of Contents and pp. 49-59, 124-183, 191-197, 345, and 364-366. (No copy available).
Shaw et al., "Optomechanical design of tunable Ip-based Fabry-Perot filters for WDM applications", Journal of Microlithography, vol. 4, Oct.-Dec. 2005, pp. 041303-1-041303-8. (no copy available).
Seamer et al., "Sheath Fluid control to Permit Stable Flow in Rapid Mix Flow Cytometry", Cytometry, vol. 5699, 2005, pp. 75-79.
Singh et al., "Analysis of cellular Structure by Light Scattering Measurements in a New Cytometer Design Based on a Liquid-Core Waveguide", IEEE Proceedings Nanobiotechnology, vol. 151, No. 1, Feb. 2004, pp. 10-16. (abstract only).
Singh et al., "Leaky ARROW Waveguides for Optical Chemical and Biosensors", 1998. (no copy available).
Sivaprakasam et al., "Multiple UV Wavelength Excitation and Fluorescence of Bioaerosols", $2^{nd}$ Joint conference on Point Detections, Williamsburg, VA 2004, 10 pages.
Spear et al., "Low noise position sensitive detector for optical probe beam deflection measurements", Rev. Sci. Instrum., vol. 67, No. 7, Jul. 1996, pp. 2481-2484. (abstract only).
SRU Biosystems, Inc., "BIND Biosensor TM Technology", Apr. 3, 2004 excerpt, 1 page.
Udd, "Good Sense", SPIE's OEMagazine, Aug. 2002, pp. 27-29.
Vogel, "Tunable Liquid Crystal Fabry-Perot Filters", Institute for Electrical and Optical Communication Engineering, University of Stuttgart, 2002, 10 pages. (abstract only).
Vollmer et al., "Multiplexed DNA Quantification by Spectroscopic Shift of Two Microsphere Cavities", Biophysical Journal, vol. 85, Sep. 2005, pp. 1974-1979.

(56) References Cited

OTHER PUBLICATIONS

Weismann et al., "Singlemode polymer waveguides for optical backplanes", Electronics Letters, vol. 32, No. 25, Dec. 5, 1996, pp. 2329-2330. (abstract only).
Wippich et al., "Tunable and Fiber-Bragg-Grating Sensors", The Industrial Physicist, Jun./Jul. 2003, pp. 24-27. (no copy available).
File History for U.S. Appl. No. 13/113,021 as retrieved from the U.S. Patent and Trademark Office.
"Lab-on-a-Chip, Advances in Microarray Technology and Advances in Biodefense Technology", brochure, May 7-8, 2008, 6 pages. (No copy available).
Sims et al., "Analysis of Single Mammalian Cells On-Chip", Lab Chip., vol. 7, Issue 4, Apr. 2007, pp. 423-440. (Abstract only).
File History for U.S. Appl. No. 12/022,485 as retrieved from the U.S. Patent and Trademark Office.
File History for U.S. Appl. No. 12/023,436 as retrieved from the U.S. Patent and Trademark Office.
File History for U.S. Appl. No. 12/025,394 as retrieved from the U.S. Patent and Trademark Office.
File History for U.S. Appl. No. 11/698,338, as retrieved from USPTO.
File History for U.S. Appl. No. 13/113,021, as retrieved from USPTO.
File History for EP Application No. 09151643.5 as retrieved from the European Patent Office electronic file system on Aug. 14, 2013, 149 pages.
File History for EP Application No. 08150482.1 as retrieved from the European Patent Office electronic file system on Aug. 29, 2013, 82 pages.
File History for U.S. Appl. No. 13/206,436 as retrieved from the U.S. Patent and Trademark Office.
File History for U.S. Appl. No. 13/206,439 as retrieved from the U.S. Patent and Trademark Office.
File History for U.S. Appl. No. 11/698,338 as retrieved from the U.S. Patent and Trademark Office.

\* cited by examiner

METHOD AND SYSTEM IMPLEMENTING SPATIALLY MODULATED EXCITATION OR EMISSION FOR PARTICLE CHARACTERIZATION WITH ENHANCED SENSITIVITY

CROSS REFERENCE TO RELATED PATENTS AND APPLICATIONS

This application is related to U.S. application Ser. No. 11/698,338, entitled "Method and System for Evaluation of Signals Received from Spatially Modulated Excitation and Emission to Accurately Determine Particle Positions and Distances", filed on even date herewith.

BACKGROUND

Methods for particle characterization (which generally relates to detection as well as other useful characterizations such as location/position determination, particle counting and cell sorting) often suffer from a low signal-to-noise ratio (SNR), since the signal obtained from the particle (in general: a small object) is typically weak in comparison to the background. This is particularly true in connection with optical methods of particle characterization. The low signal-to-noise ratio is also particularly noteworthy in cases of detection of individual particles such as a cell, an aerosol, a molecule, a subvolume of liquid which differs from the surrounding liquid or emulsion, or a piece of DNA with dyes or tags at selection positions.

With respect to the DNA case, conventional DNA sequencing is accomplished by splitting a DNA strand into small pieces, separating the pieces with electrophoresis and then elaborately reconstructing the DNA sequence. An alternative process has recently been developed. In this alternative process, certain base sequences are tagged with fluorescent dyes. After stretching (or "linearizing") the molecule, the DNA strand is moved through a microfluidic channel at a constant speed. A special fluorescence reader with a high spatial resolution (approx. 1 µm) is used to record the positions of the fluorescent dyes or tags. As a result, an "optical bar code" of the DNA containing the position of the tags is recorded. Therefore, the DNA sequence may be identified.

Typical distance between the tags along the DNA is several µm. Consequently, the required spatial resolution is one µm or better. Typically, this concept is demonstrated by using a con-focal microscope, which allows for exciting and also detecting the fluorescence within a very small volume (~1 µm3).

FIG. 1 schematically illustrates a conventional approach for spatially resolved fluorescence excitation. As shown, a system 10 includes a detector 12, a channel 14 and an excitation light 16. A small volume within the channel 14 is excited. Light is collected from the excited volume. DNA strings 20 with tagged portions 22 run through an excitation area 24 of the channel 14. The positions of the tags are calculated using a time dependent detector signal.

This approach has been successfully implemented. However, it requires sophisticated and bulky optics to ensure suitably sized excitation and detection volumes. Moreover, the resultant signal-to-noise ratios are lower than desired.

INCORPORATION BY REFERENCE

U.S. application Ser. No. 11/698,338, entitled "Method and System for Evaluation of Signals Received from Spatially Modulated Excitation and Emission to Accurately Determine Particle Positions and Distances", filed on even date herewith, is hereby incorporated herein by reference in its entirety.

BRIEF DESCRIPTION

In one aspect of the presently described embodiments, the method comprises generating a spatially modulated excitation region, creating relative movement between a particle and the excitation region, the particle being excited upon exposure to the excitation region to obtain a time modulated signal, and, recording the modulated signal.

In another aspect of the presently described embodiments, the excitation region includes an excitation pattern.

In another aspect of the presently described embodiments, the time modulated signal is caused by light emission from the particle.

In another aspect of the presently described embodiments, the excitation region comprises interference stripes.

In another aspect of the presently described embodiments, the excitation region is generated by at least one of a shadow mask and a lens array.

In another aspect of the presently described embodiments, the excitation pattern is generated by chemo-luminescence.

In another aspect of the presently described embodiments, the method further comprises at least one of determining a location of the particle based on the signal, counting particles based on the signal, and sorting particles based on the signal.

In another aspect of the presently described embodiments, the detecting comprises detecting with a pixilated detector.

In another aspect of the presently described embodiments, the particle is a portion of a DNA molecule or a molecule attached to the DNA molecule and the signal is used to determine DNA sequencing.

In another aspect of the presently described embodiments, the detecting comprises using a spectrometer to receive the fluorescent spectrum of the fluorescing analyte.

In another aspect of the presently described embodiments, the generating of the excitation region comprises generating a spatially modulated pattern based on at least one of geometry, electric or magnetic field, fluorescence quenching, analyte concentration, density, and acoustic standing wave.

In another aspect of the presently described embodiments, the generating of the excitation pattern comprises generating a spatially modulated region based on environment.

In another aspect of the presently described embodiments, the generating, creating and recording is conducted in two-dimensions to locate the particle.

In another aspect of the presently described embodiments, a method for characterizing particles comprises moving a particle within a channel, providing an environment along the channel which causes the particle to create a time modulated signal, and, detecting and evaluating the time modulated signal.

In another aspect of the presently described embodiments, the environment comprises an optical element and the particle emits light detected by the optical element.

In another aspect of the presently described embodiments, the optical element is operative to modulate the signal obtained from the particle as a function of a position of a particle.

In another aspect of the presently described embodiments, the method further comprises moving the optical element.

In another aspect of the presently described embodiments, the optical element is one of a shadow mask and a micro-lens array.

In another aspect of the presently described embodiments, the method further comprises at least one of determining a location of the particle based on the signal, counting particles based on the signal, and sorting particles based on the signal.

In another aspect of the presently described embodiments, the detecting comprises detecting with a pixilated detector.

In another aspect of the presently described embodiments, the particle is a portion of a DNA molecule or a molecule attached to the DNA molecule and the signal is used to determine DNA sequencing.

In another aspect of the presently described embodiments, the detecting comprises using a spectrometer to receive a fluorescent spectrum of the particle.

In another aspect of the presently described embodiments, the optical element is operative to pattern the light based on at least one of geometry, electric or magnetic field, fluorescence quenching, particle concentration, density, and acoustic standing wave.

In another aspect of the presently described embodiments, a system for characterizing particles comprises means for generating a spatially modulated excitation region, means for providing relative movement between a particle and the region, the particle being excited upon exposure to the excitation area to obtain a time modulated signal, means for recording the modulated signal.

In another aspect of the presently described embodiments, the system further comprises at least one of a means for determining a location of the particle based on the signal a means for counting particles based on the signal, and means for sorting particles based on the signal.

In another aspect of the presently described embodiments, a system for characterizing particles comprises a channel, a means for moving a particle within the channel, an environment along the channel operative to cause the particle to create time modulated signal, and, a detection system to record and evaluate the time modulated signal.

In another aspect of the presently described embodiments, the environment comprises an optical element.

In another aspect of the presently described embodiments, the system further comprises an anti-resonant waveguide operative to cause the particle to emit light.

In another aspect of the presently described embodiments, the system further comprises at least one of a means for determining a location of the fluorescent analyte based on the signal, a means for counting particles based on the signal, and a means for sorting particles based on the signal.

In another aspect of the presently described embodiments, the environment allows for a two-dimensional evaluation.

DETAILED DESCRIPTION

This patent application describes a method and a system to improve the signal-to-noise ratio during particle characterization by implementing a phase sensitive technique which allows for clearly distinguishing between the signals from the particle and the background. The method is based on the deliberate introduction of controlled relative movement between the particle and the environment. The combination of, for example, the moving particle and a conditioned environment results in a time modulated signal. A monitored response comprises a noisy background signal and the modulated signal, with a well defined time dependence attributable to the particle. Both hardware and software solutions can be applied to extract the signal attributed to the particle.

It should be understood that the signal attributed to the particle can then be used in characterizing the particle for a variety of different applications, including detection, location/position determination, and cell sorting. Various techniques may be employed to accomplish these characterizations. It should be noted, however, that one technique for characterization, i.e., determination of particle positions and distances, is described in U.S. application Ser. No. 11/698,338, entitled "Method and System for Evaluation of Signals Received from Spatially Modulated Excitation and Emission to Accurately Determine Particle Positions and Distances," filed on even date herewith, and may be advantageously implemented along with the presently described embodiments.

It will be appreciated that the contemplated signal can have any shape as a function of time. It is not necessarily periodic. Even a signal modulated randomly is useful, as long as the structure of the signal is known. In this regard, the structure may be known but the signal may not follow an analytic regularity. So, the time periods defining "on" and "off" states for the particle will have a random length. Even where the time dependence of the signal is built into the system, the time dependence of the system can be varied, as long as it is predictable or known.

Note that different encodings of the signal (e.g., chirped or strictly periodic) carry specific advantages for a particular application. Chirped signals improve spatial resolution and particle separation. Strictly periodic signals allow for determining particle speed and are more adaptive to particles with different speeds.

Figure 12:
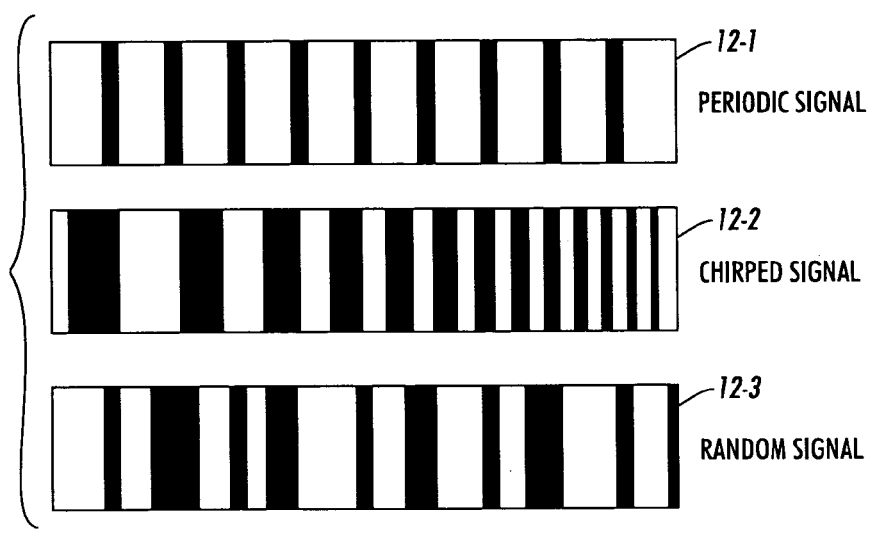
FIG. 12 is an illustration of various forms of signals that may be used in connection with the presently described embodiments.

To explain, with reference to FIG. 12, various types of signals are illustrated. For example, signal 12-1 is a periodic signal. Signal 12-2 is a chirped signal, e.g., a signal that has a linearly increasing frequency. Also shown is a random signal 12-3. It should be appreciated that these signals (as well as others) may be used in connection with the presently described embodiments to achieve the objectives of the presently described embodiments.

The presently described embodiments are described for a variety of cases including: (1) a collection of individual moving particles (2) a linearized DNA strand in which the objects of interest are distributed and fixed along the length of the strand i.e., commonly termed DNA sequencing, and (3) a collection of particles potentially fixed on a surface (providing a need, in some applications, for a two-dimensional analysis).

In this regard, the particles being detected may include cells, aerosols, DNA material pieces of DNA with dyes at selected positions, subvolumes in a liquid which differs from the surrounding liquid or emulsion, droplets, other small volumes of fluid, bubbles, single molecules, agglomerated molecules, molecule clusters, biological cells, viruses, bacteria, proteins, microparticles, nanoparticles, and emulsions. A droplet or small volume of fluid may, for example, include atoms, molecules or other particles that affect refractive index, absorption, or other optical characteristics. An object "travels" or is caused "to travel" if the object moves through a succession of positions. For example, the object could be conveyed in a fluid, such as a liquid, gas, or aerosol, in which case the object may be referred to as being "carried by the fluid." Still further, it should be appreciated that a channel may be defined in a variety of manners to include not only ones defined by walls, but also ones defined by the flow of particles in, for example, an aerosol stream or the like.

It should be further understood that light emission from these particles may result from a variety of sources including fluorescence excitation, elastic and inelastic light scattering, chemo-luminescence or other types of light scattering and reflection techniques. Still further, the light used in these implementations may include a variety of different types of lighting including, ultraviolet, VIS, infrared, near infrared, etc. As will be described in greater detail below, the environments in which this particle characterization process is implemented include environments wherein there is a spatially modulated excitation of the particles or a modulation of an emitted light from particles over a detection region. In this regard, the particles may emit a homogeneous excitation that is filtered using, for example, a shadow mask or other optics, which leads to a spatial modulation of the emitted light.

It should also be understood that the presently described embodiments may be applied to optical as well as non-optical environments such as those involving capacitance, induction, resistivity, etc. FIGS. 2-14 generally relate to optical cases while FIG. 15 relates to an example non-optical case.

Figure 1:
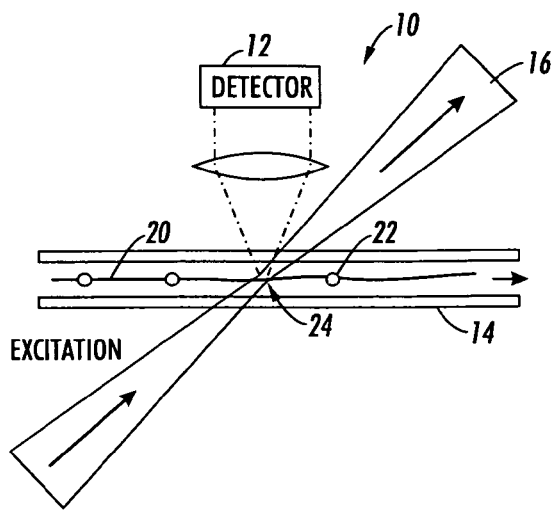
FIG. 1 is a representative view of a prior art system.
Figure 2:
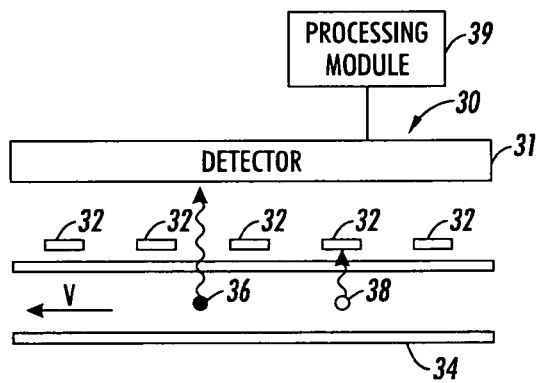
FIG. 2 is a representative view of a presently described embodiment.

With reference now to FIG. 2, a system 30 is illustrated. In the system 30, a channel 34 is provided with optical elements 32 for modulating emitted light within a detection region. The optical elements 32 may take a variety of forms such as lenses, masks or filters. Also shown is a detector 31 for detecting the emitted light from the optical elements 32 as a function of time. It should be understood that the detector 31 (as well as other detectors noted herein) may take a variety of forms including photo-diodes, avalanche photo-diodes, photo-multiplier tubes, etc. It should also be appreciated that the detector 31 and optical elements 32 may be combined in a single element or system.

Light may be emitted from particles such as particle 36 and particle 38 that are traveling down the channel 34. It should be understood that the light emission from the particle may result from the various phenomenon described above. It should also be understood that the relative movement between the particles 36 and 38 and the optical element system 32, or output modulator, create the modulation desired to be able to appropriately analyze the particles 36 and 38. The spatially modulated optics create a time modulated signal in the detector 31. This signal, which as noted may take a variety of predictable forms, may be analyzed using the processing module 39 for purposes of characterizing the particles.

As noted, the signal generated as a function of time may take a variety of forms, e.g., periodic, chirped, random . . . etc., as a function of a variety of environmental factors. In one form, that may be applied to this embodiment as well as the embodiments of FIGS. 3 and 4, the optics may take a form that coincides with the type of signal. So, the optical element structure may resemble that of the signal examples of FIG. 12.

It should be appreciated that the relative movement may be created by way of the particle moving, the detector/optical elements moving along, for example, the channel or by way of movement of both of these elements. It should be further understood that movement of both of the elements may, in one form, result in movement of each element at different velocities.

Figure 3:
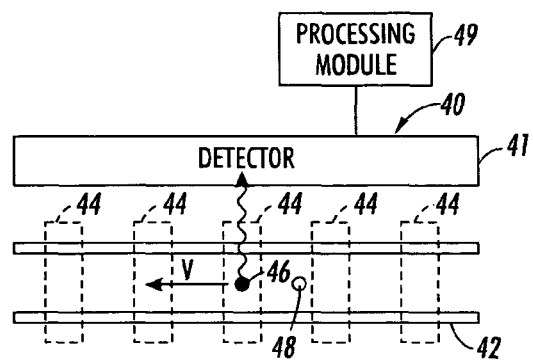
FIG. 3 is a representative view of a presently described embodiment.

With reference now to FIG. 3, a system 40 is shown. The system 40 includes a channel 42 that is provided with regions 44 where particles, such as particles 46 and 48, are caused to emit light. Regions 44, as shown, create a modulated excitation area that can be achieved by various methods. These methods include interference, use of shadow masking, use of lens arrays and use of chemo-luminescence and fluorescent quenching. Relative movement between the particle and the excitation area or pattern can be achieved by moving the particle, the excitation pattern or both. As with the previous embodiment, it should be appreciated that movement of both, in one form, would result in movement of each at different speeds. The spatially modulated optics create a time modulated signal in the detector 41. This signal, which as noted may take a variety of predictable forms, may be analyzed using the processing module 49 for purposes of characterizing the particles.

Figure 4:
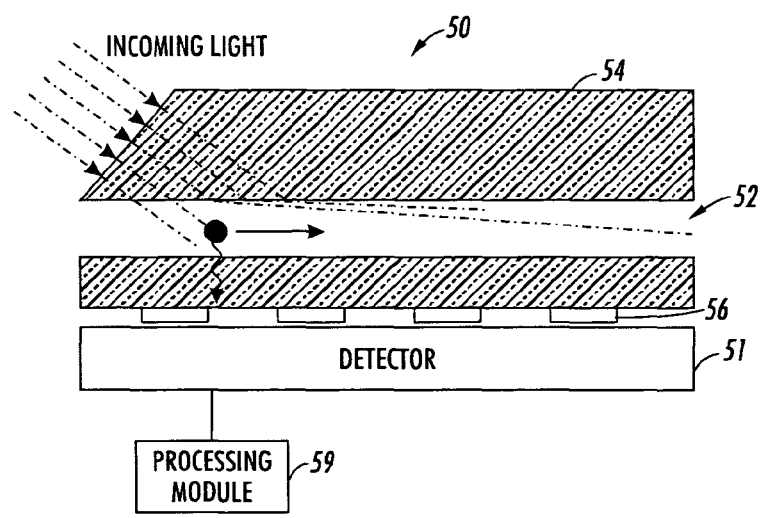
FIG. 4 is a representative view of a presently described embodiment.

With reference now to FIG. 4, a system 50 is illustrated. System 50 includes a channel 52 and an anti-resonant wave guide 54. The anti-resonant wave guide provides homogeneous illumination of the channel as the particle travels there-through. Modulation can be created by mirrors 56 which can be suitably placed inside or outside the channel. Again, the spatially modulated optics create a time modulated signal in the detector 51. This signal, which as noted may take a variety of predictable forms, may be analyzed using the processing module 59 for purposes of characterizing the particles.

It should be apparent from the embodiments described in connection with FIGS. 2-4, the presently described embodiments provide for a characterization of particles traveling through other types of medium (e.g., liquid) that is improved by way of modulation. In some cases, the light emitted from particles is modulated and, in other cases, the modulation occurs by way of modulated excitation of the particles. In both cases, it is the relative movement of the system elements that provides the modulated effect.

Figure 11:
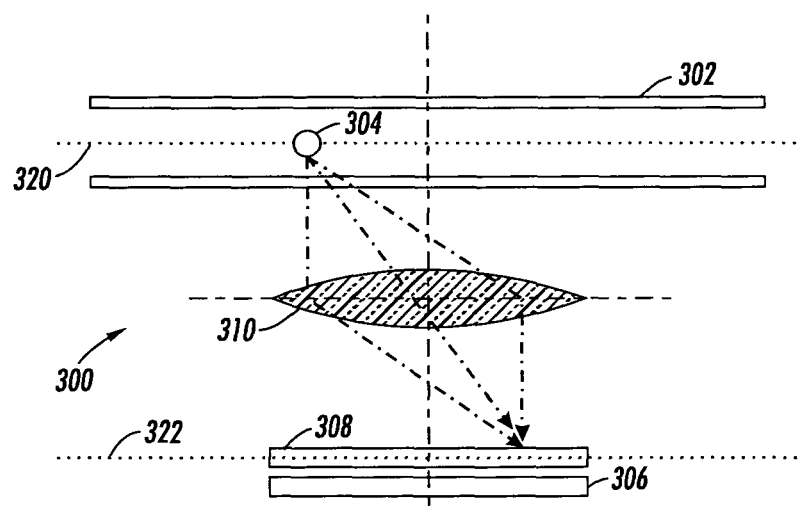
FIG. 11 is a representative view of a presently described embodiment.

With reference to FIG. 11, another embodiment is illustrated. Of course, various configurations involving the imaging of a particle to a detector plane are contemplated. However, one such example as shown includes a system 300 positioned near a channel 302 in which a particle 304 is traveling. The particle 304 is detected by a detector 306 having an optical element 308 positioned thereon operative to produce a spatial pattern. The detection of the particle is facilitated by optics 310, which may take a variety of forms including a lens or lens system. The particle lies in an object plane 320 while an image plane 322 is associated with the detector 306 and optical element 308.

In this arrangement, the particle size, pattern size and spatial resolution are essentially de-coupled. In this regard, the optics 310 serve to magnify (or de-magnify) the particle 304 and conduct the detecting at a location remote from the particle 304. As shown, light originating from the particle 304 is modulated in the image plane 322. The detector 306 is then able to detect the light from the particle 304 in the channel 302 without being positioned on the channel 302. Using this configuration, the optical element 308 should be in or near the image plane 322 of the optics 310. In this way, the "optical distance" between the particle 304 and the optical element 308 is minimized. It should be appreciated that the detector itself can contain optics as well as introduce additional magnification or de-magnification. In addition, the size of the detector is a factor in the sampling rate of the system. In some cases it might therefore be preferable to de-magnify the channel on a small and faster detector to gain increased sampling rate.

Further, the optical element may be positioned on the channel itself. If so, the distance between the detector and the optical element would be determined by the channel dimensions.

Figure 5:
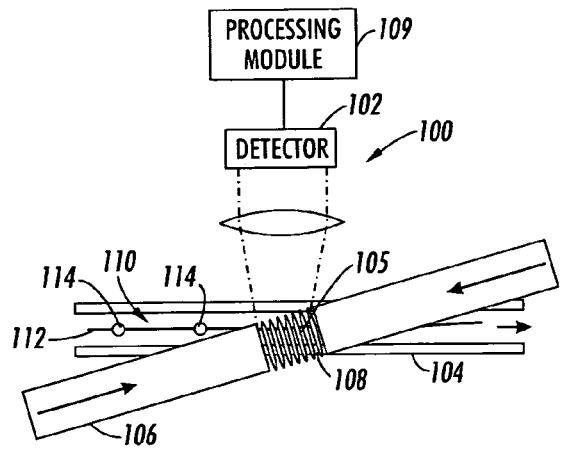
FIG. 5 is a representative view of a presently described embodiment.

A more specific implementation of the presently described embodiments relates to DNA sequencing. With reference to FIG. 5, a system 100 according to the presently described embodiments is shown. The system includes a detector 102, a fluid channel 104 and excitation light 106 having a spatially modulated excitation pattern 108 therewithin. The pattern 108 aligns with the channel 104 to create a detection region or area 105. The system 100 allows for conveyance of, for example, a DNA string 110 having a backbone portion 112 and fluorescent tags, or particles, 114 embedded therein. In at least one form, the interference pattern 108 is generated by an energy source such as a laser source and has a submicron periodicity perpendicular to particle flow. It should be appreciated that other angles might also be used. As a fluorescent particle 114 moves down the channel 104 through the pattern 108, the fluorescent emission is modulated according to the speed of the fluorescent particle or tag 114 and the periodicity of the stripe pattern 108. The signal detector 102, which records the emission over at least one stripe can be used. The detected signal is recorded with a fast detector read-out in order to capture the "blinking" of the fluorescent particle(s) or tags 114 while they are moving through the detection area 105 and, consequently, the excitation pattern 108. As shown, a processing module 109 may be implemented to analyze the signal for purposes of particle characterization.

The presently described embodiments enable fluorescence detection with high signal-to-noise ratio and high spatial resolution, as discussed in the following, without the need of expensive and bulky optics.

Figure 6:
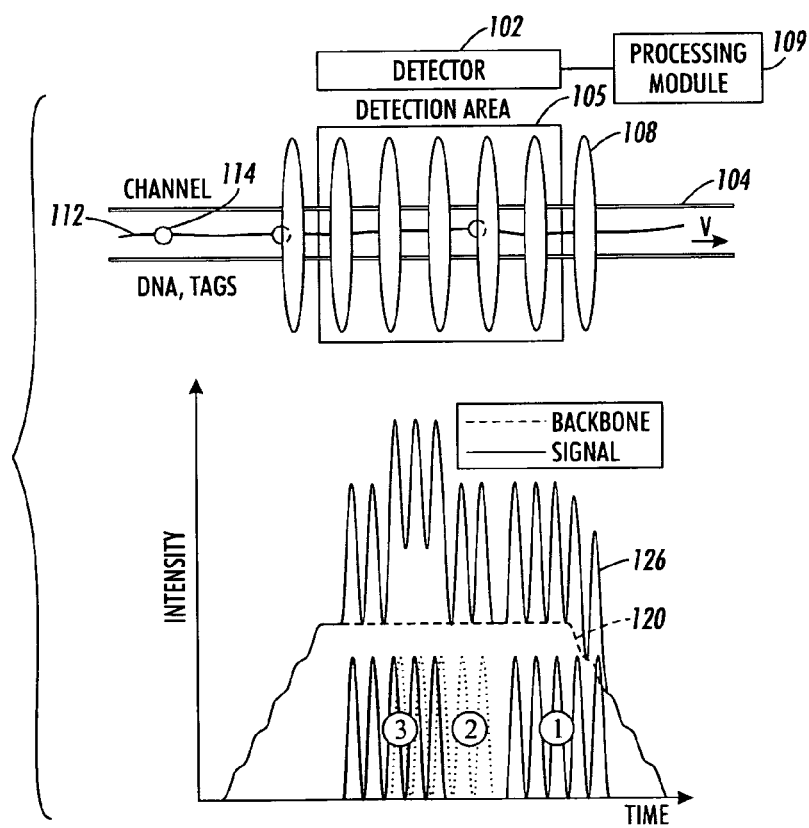
FIG. 6 is a representative view of a presently described embodiment.

In the particular application contemplated, the DNA backbone 112 is typically labeled with one type of fluorophore and specific portions of the linearized molecule are labeled with a second type of fluorophore, that is, fluorescent tags 114. FIG. 6 illustrates the detection scheme according to the presently described embodiments in more detail. As shown, the fluorescence backbone signal 120 first increases in a step-like function when the uniformly labeled DNA backbone 112 moves into the detection area 105. Additionally, the backbone signal 120 is superimposed with a sinusoidal signal 122 when one of the tags 114 moves through the excitation pattern 108. This results in a detected signal 126.

In the exemplary embodiment illustrated in FIG. 5, only a single detector is shown. However, multiple detectors may be implemented. Also, it should be appreciated that various configurations of detectors may be implemented to realize the presently described embodiments.

Figure 7:
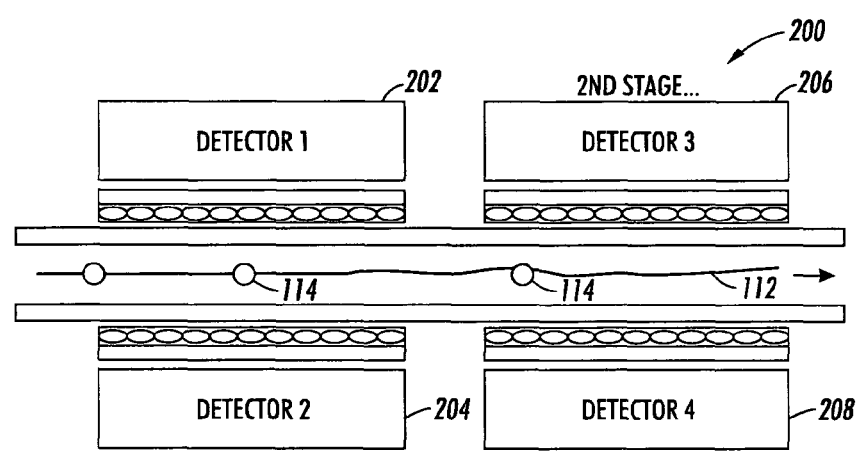
FIG. 7 is a representative view of a presently described embodiment.

In this regard, with reference now to FIG. 7, a system 200 wherein it might be favorable to detect the tagged portions 114 and the DNA backbone 112 with different detectors is shown. Backbone portions 112 and tagged portions 114 are usually labeled with fluorophores emitting at different wavelength bands. Appropriate filters ensure that only fluorescence originating from the tags enters detector 202 whereas detector 204 receives light only from the backbone. Simple optical components can be incorporated to improve wavelength selectivity of the filters. For example, micro-lens arrays can collimate the fluorescent light. The filters can be designed such that they do not only transmit the first wavelength band of interest but also efficiently reflect the second wavelength band of interest onto the opposite detector in order to minimize fluorescent light loss. The system 200 of FIG. 7 can also be used to measure the fluorescence from different fluorescence tags marking different portions of the DNA simultaneously.

Also, it should be appreciated that second stage detectors 206 and 208 may likewise be implemented to refine, for example, the DNA analysis that is being conducted. For example, to refine a DNA characterization, fluorescence from differently colored tags marking different portions of a DNA strand may be measured.

Figure 8:
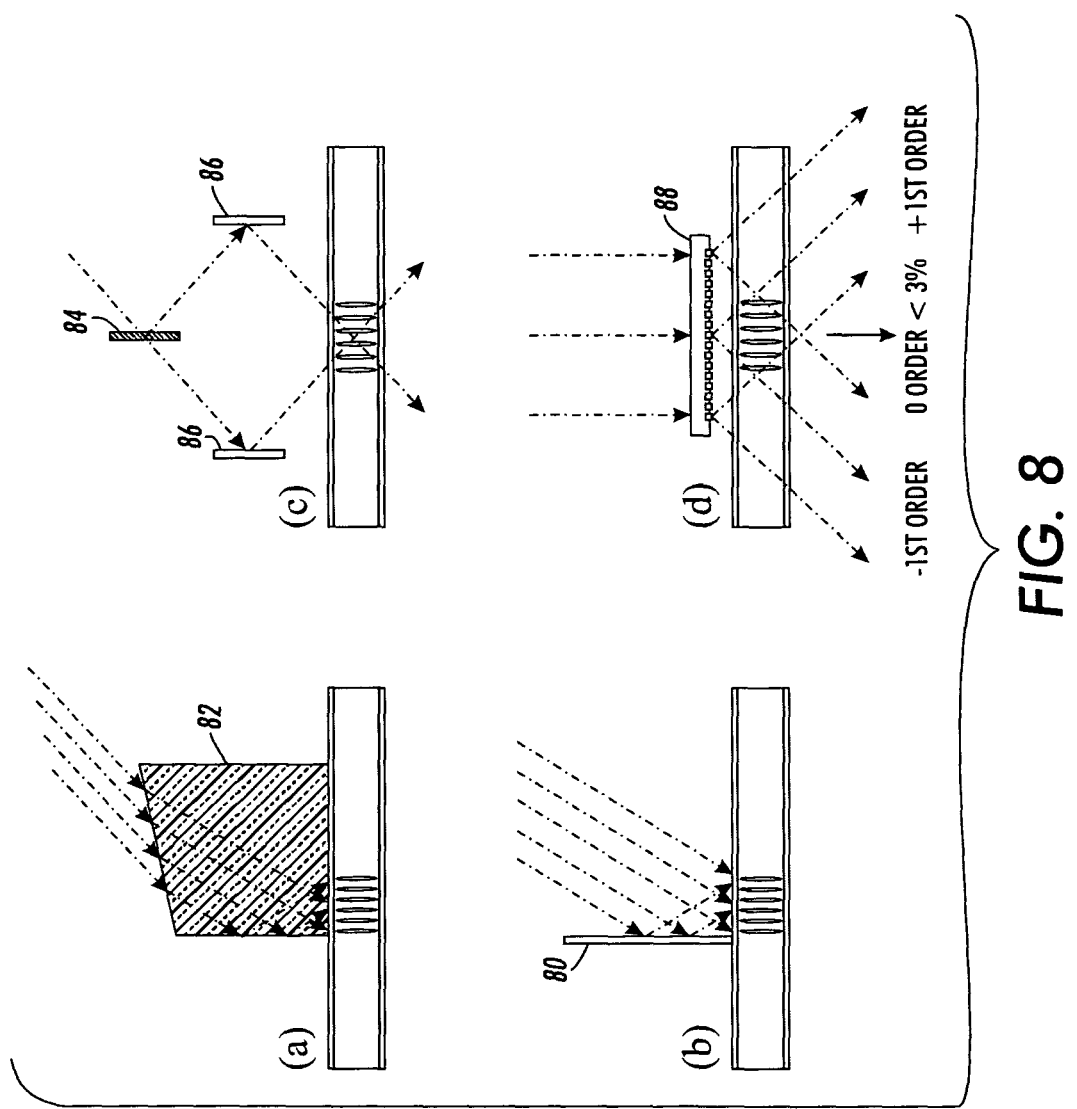
FIGS. 8(a)-(d) are representative views of presently described embodiments.

To generate a suitable pattern, several well known techniques can be applied to create, for example, an interference pattern as depicted in FIGS. 8(*a*)-(*d*). Stripes are usually generated by creating a standing wave in one dimension. For example, in FIG. 8*b*, a mirror 80 creates a standing wave in the channel direction. Different directions also may be used. The distance d between two adjacent interference maxima can be calculated as follows:

$$d \frac{\lambda}{2\sin\alpha},$$

where α indicates the relative angle between the two interfering beams and λ is the wavelength, with d varying between λ/2 and infinity dependent upon α.

In general, the excitation pattern can be directed onto the channel "from outside" through the top or bottom surface or "in plane" from the side. As the detection components are most probably attached from top and/or bottom it is favorable to use "in-plane" excitation in order to reduce the amount of excitation light that reach the detectors.

All of the interferometer techniques shown in FIG. 8(a)-(d) can be realized in the microfluidic chamber by using waveguide structures and mirrors based on total internal reflection (TIR) on substrate/air interfaces. FIG. 8(a) illustrates a prism interferometer. FIG. 8(b) illustrates a Lloyd interferometer using the mirror 80. FIG. 8(c) illustrates a Michelson interferometer using a beam splitter 84 and mirrors 86. In order to achieve an even higher signal-to-noise ratio it would be feasible to periodically move the interference pattern in the channel direction. This can be achieved by mounting a mirror as shown in FIG. 8(c) onto a periodically moving stage (e.g., a speaker or piezo element). This technique can also be applied to address stationary particles. This allows improvement in the sensitivity of the system by using a double modulation technique.

Figure 10:
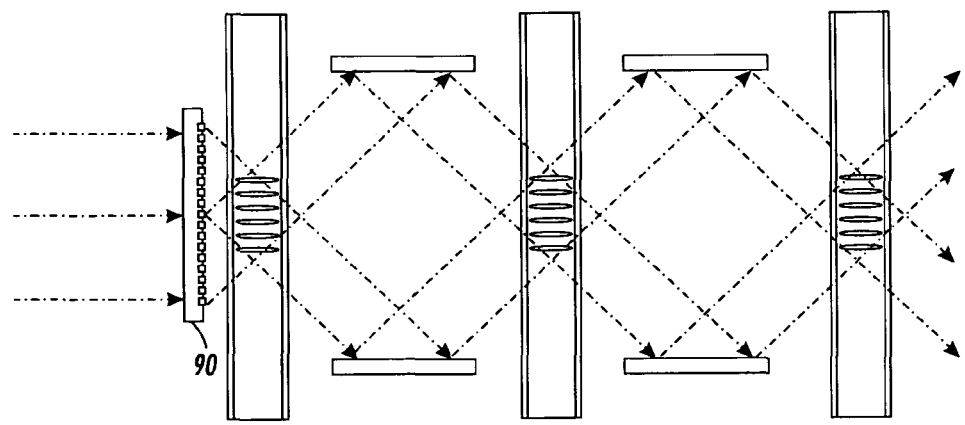
FIG. 10 is a representative view of a presently described embodiment.

Last, FIG. 8(d) illustrates a phase mask interferometer 88. A favorable approach is based on phase masks or transmission gratings, as shown in FIG. 8(d). Light scattered into the −1st order interferes with light scattered in +1st order. The gratings can be designed such that scattering into 0 and 2nd order is minimized. Most techniques shown in this section can be designed such that multiple-fluidic-channel excitation is feasible. FIG. 10 illustrates another design for illuminating parallel channels which is based on phase masks, such as phase mask 90.

Having thus described example systems incorporating the teachings of the presently described embodiments, it should be understood that the methods according to the presently described embodiments include, in at least one form, the basic undertakings of creating a spatially modulated environment, detecting light emitted from the excited particles in the environment, and generating a time modulated signal based on the detecting. In at least one form, the generated signal is used to determine positions of the excited particles, e.g. tags in the DNA strand. The system, in one form, is provided with a processing module (e.g., processing modules 39, 49, 59 and 109) to allow for the generation of the spatially modulated signal and any subsequent processing such as determining the relative positions of particles. This processing module may be incorporated within the detector or implemented apart from the detector. Along these lines, it should be understood that the methods described herein may be implemented using a variety of hardware configurations and software techniques. For example, the contemplated processing module may include software routines that will allow for signal generation and location determination.

Figure 9:
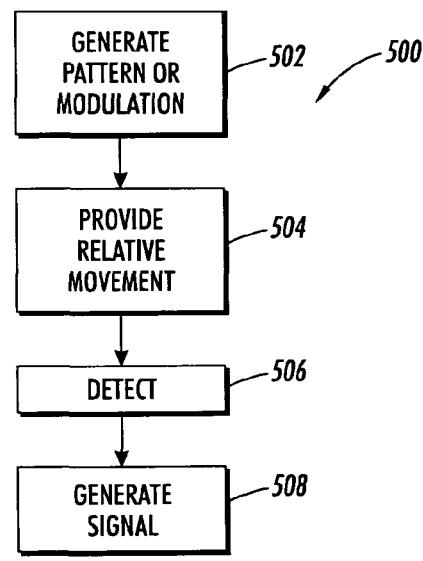
FIG. 9 is a flow chart according to the presently described embodiments.

With reference now to FIG. 9, a method 500 according to at least one of the presently described embodiments is illustrated. Initially, an excitation pattern is generated (at 502). As noted, the excitation may be homogeneous with a patterned output generated by a shadow mask or the like (e.g., a modulator). Next, relative movement between, for example, a fluorescing analyte and the excitation pattern is provided (at 504). Any emitted or scattered light as function of time is then detected (at 506). A spatially modulated signal based on the detecting is then generated (at 508). As noted above, the spatially modulated signal can then be used, in one form, to determine the relative positions of fluorescing particles such as tags in a DNA strand.

With respect to detection of a signal relating to the fluorescent emissions as with the DNA implementation, the modulated excitation not only ensures high spatial resolution but at the same time enables a method to increase the signal-to-noise ratio. Most sources which contribute to the background signal (e.g., the backbone signal, fluorescence excited by scattered excitation, or all other DC-like sources) are eliminated by a correlation technique, which allows the read-out to be only sensitive to the modulated signal originating from the moving tags. Considering a tag-speed of 15 m/ms (or mm/s), an a periodic excitation pattern with a stripe width of 1 m and a size of the tagged portion considerably less than the excitation stripe, results in a transit time of approximately 70 s per period. This results in a modulation of the fluorescence signal in the order of 10 kHz. Additionally, the excitation source can be modulated with a higher frequency in order to separate fluorescence light from other background sources (e.g., room light). The frequency has to be chosen high enough to ensure that the light source is switched on and off several times while a tag is passing one interference fringe. A modulation frequency of 100 kHz fulfills that criterion and is easily feasible. As much faster detectors are available, it is even possible to apply conventional lock-in or correlation techniques to sample more accurately at 100 kHz, e.g., by modulating the excitation light with 1 MHz in phase with a detector.

It should be understood that, in at least one form of the presently described embodiments, in order to determine the precise position of the tags on the DNA, the detector signal (no matter how obtained) is de-convoluted. The signal is recorded with a high sampling rate. The time information is thus converted to position information using the velocity of the DNA string. In the case of a strictly periodic excitation pattern, the velocity of the DNA string is extracted from the periodicity of the time dependent fluorescence signal or can be measured by other well known techniques. The analysis can be done, using a variety of signal processing algorithms including Fourier-Transformation analysis or Least-Square fitting techniques. Some of these techniques are described in greater detail in, for example, U.S. application Ser. No. 11/698,338, entitled "Method and System for Evaluation of Signals Received from Spatially Modulated Excitation and Emission to Accurately Determine Particle Positions and Distances", filed on even date herewith, which is hereby incorporated herein by reference in its entirety.

Figure 16:
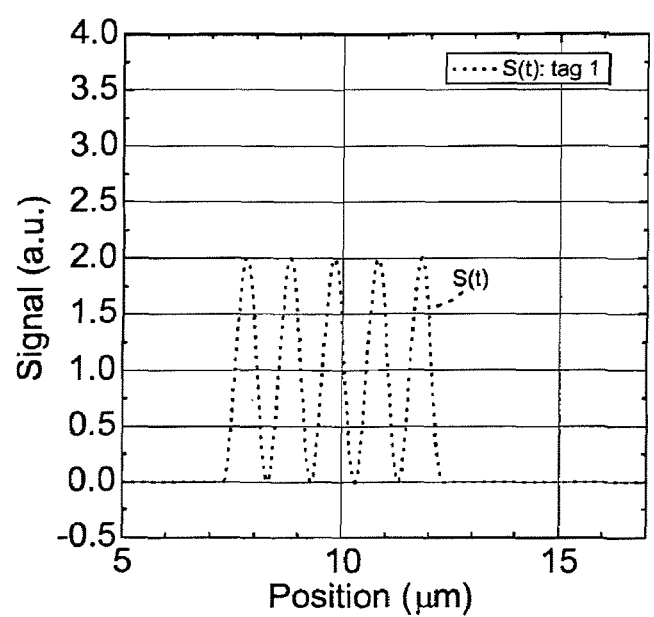
FIG. 16 is a graph illustrating a signal from a particle detected with a system in accordance with some embodiments.
Figure 17:
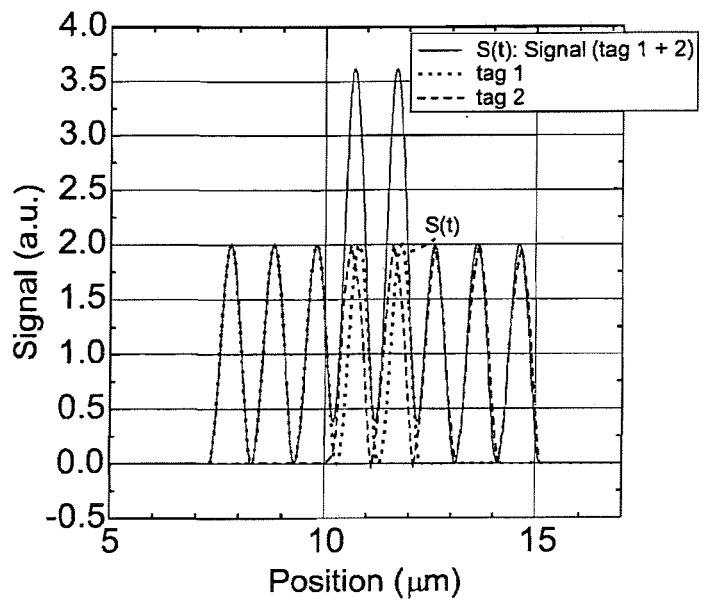
FIG. 17 is a signal from two particles detected with a system in accordance with some embodiments.
Figure 18:
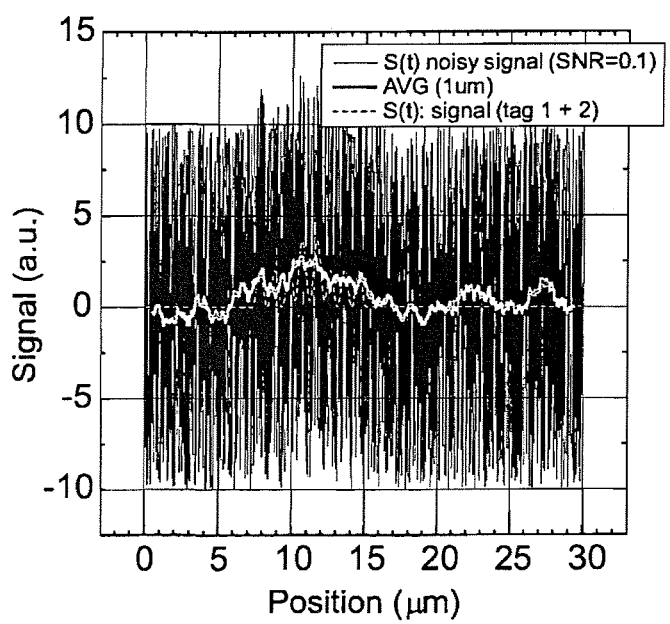
FIG. 18 is a signal from two particles where noise is present in the signal.

An exemplary procedure for the signal processing is as follows: The time-dependent signal S(t) corresponding, for example, to the spatial modulation of the excited tags (shown in various forms in FIGS. 16-18), is multiplied with a test function P(t), which is restricted to a small window in time of the signal, and subsequently integrated. The test window is then shifted by one time interval and processed in the same way again. This is done for all time intervals. The following equation describes how the resulting correlation signal L(t) is calculated.

$$L(t) = \int_{t-T}^{t} S(\tau)P(\tau - t + T)d\tau$$

Figure 19:
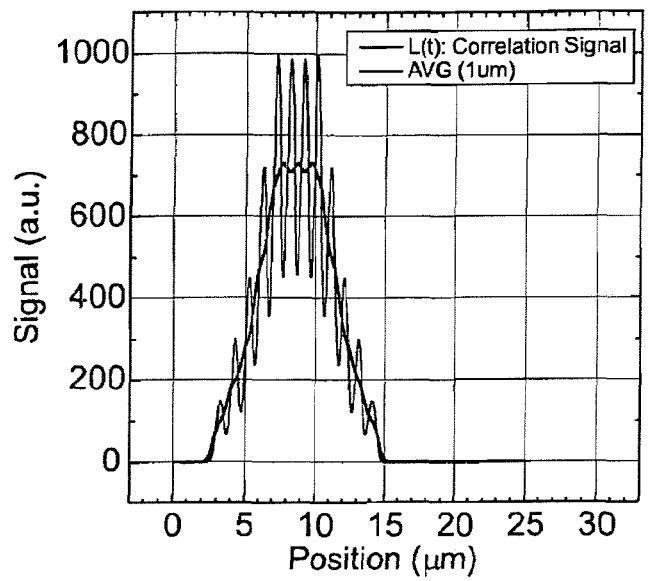
FIG. 19 is a signal used in the presently described embodiments.
Figure 20:
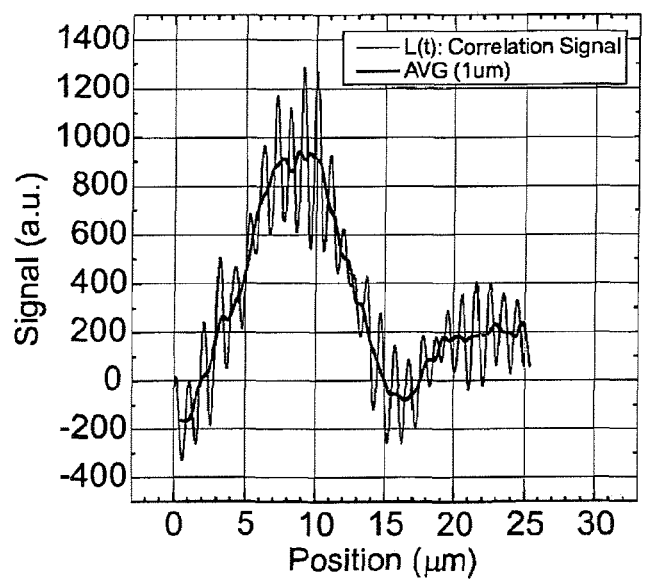
FIG. 20 is a signal used in connection with the presently described embodiments.

For the following example, a sinusoid was used as test function with a periodicity identical to the signal frequency. The integration window T was chosen to cover 5 periods of the sinusoid. FIG. 19 shows the resulting signal L(t) without noise whereas FIG. 20 shows the same evaluation with noise added to the original signal.

In order to determine the precise position of the tags on the DNA, the correlation signal is further processed. The analysis can be done, using a variety of signal processing algorithms, including Fourier-Transformation analysis or Least-Square fitting techniques. The latter one has been used in the following example.

A triangular function f(t) is fitted to the correlation signal. In this specific example, two particles are within the detection area at the same time. The correlation signal is thus fitted with the sum of two triangles. The position ($t_1$, $t_2$) of the two triangles is varied independently in order to minimize the deviations between the correlation signal and the sum of the triangle functions. In other words, t, is varied in order to minimize $\chi^2$, where i is the number of a particle with $$\chi^2 = \sum_t \left( L(t) - \sum_i f(t - t_i) \right)^2$$

Figure 21:
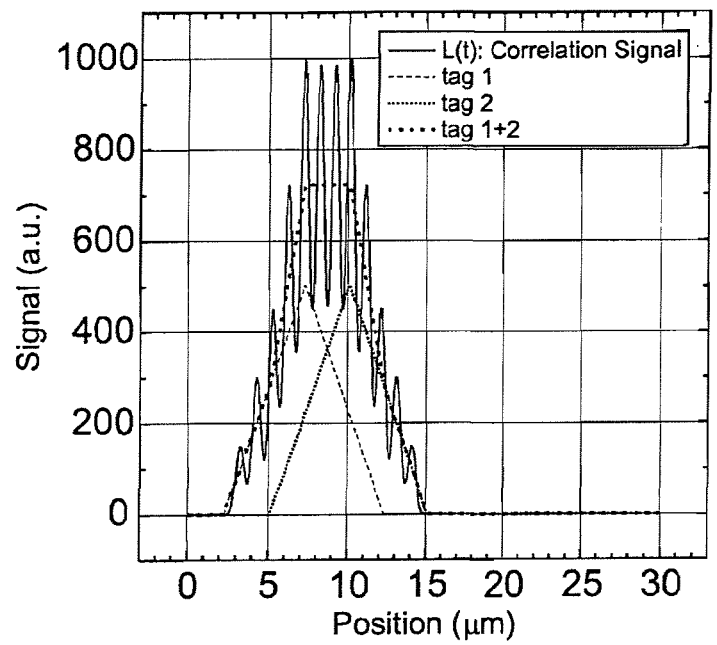
FIG. 21 is a signal shown in FIG. 19 having applied thereto the presently described embodiments.
Figure 22:
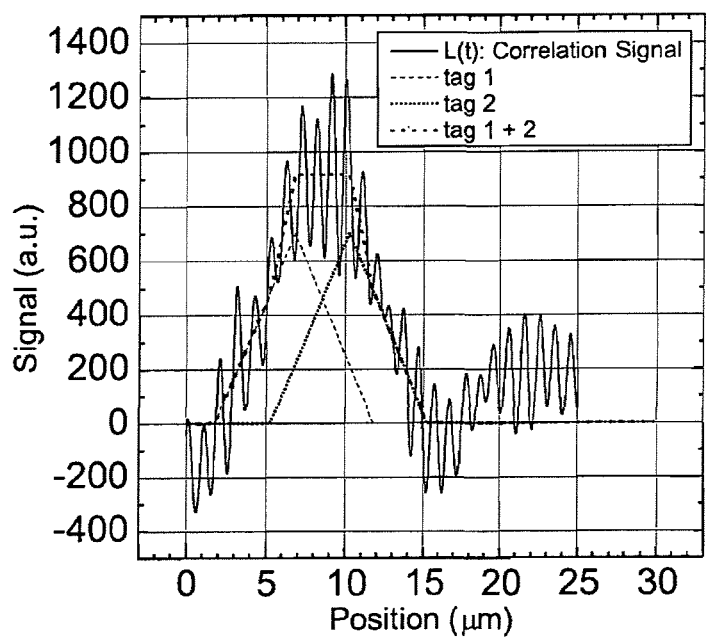
FIG. 22 is the signal of FIG. 20 having applied thereto the presently described embodiments.

FIGS. 21 and 22 shows the two triangles as well as the sum of both triangles for the case without and with noise, respectively. The position of the tip of the triangles identifies the original position of the fluorescent tags.

The following table indicates the real positions of the fluorescent tags as well as the deconvoluted positions for both discussed cases. Without noise, the positions received from the deconvoluted Signal match perfectly with the real positions of the fluorescent tags. In the noisy case, the deviation is larger but still smaller than 1, meaning that in this case the position error is still smaller that the periodic constant from the excitation pattern. This is sufficient for most applications.

|  | Real position | Position of deconvoluted signal without noise | Position of deconvoluted signal with noise (SNR=0.1) |
| --- | --- | --- | --- |
| Tag 1 | 7.30 | 7.29 | 6.80 |
| Tag 2 | 10.10 | 10.11 | 10.25 |

It should be understood that very specific choice of functions for P(t) and f(t) has been made to demonstrate this technique. Many other functions can be chosen to similarly solve the discussed problem.

According to the presently described embodiments, correlation techniques can be applied to eliminate noise from the recorded time-dependent fluorescence. Even with a SNR=0.1, signal processing is still very reliable.

Moreover, the location of a fluorescence particle can be extracted precisely from the time-dependence of the fluorescence signal (even in the case of extremely high noise). Also, the positions of several fluorescent particles which are within the interference pattern simultaneously can be determined.

As noted, the above techniques can be modified to be implemented in a variety of different circumstances. One such modification may involve generalizing the above technique to evaluate the position of a single particle that may not produce a periodic signal, but another signal with known time dependence.

Figure 23:
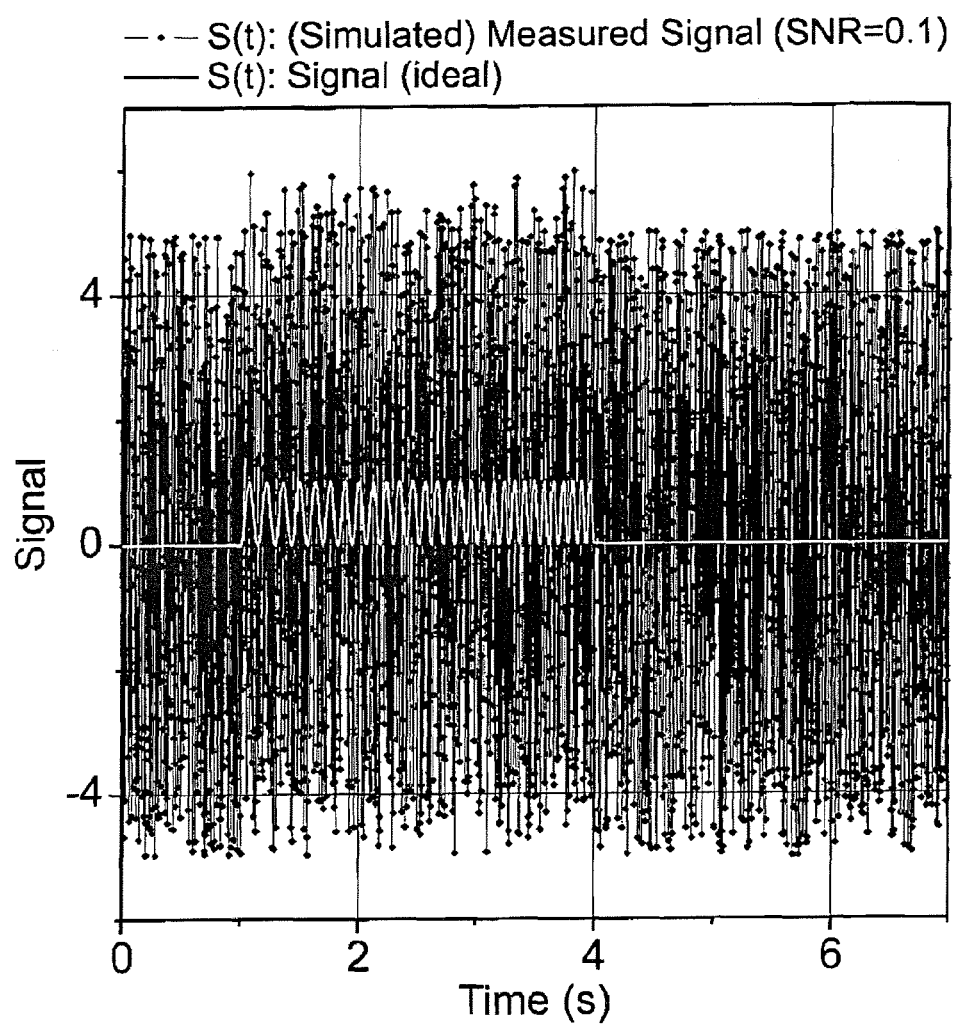
FIG. 23 is a signal used in connection with the presently described embodiments.

In this regard, with reference to FIG. 23, a chirped signal is used. In this exemplary context, the chirped signal is a non-periodic signal where the duration of each detection of light (e.g. 29 peaks) from the particle decreases by a factor of two over the entire signal length T (e.g. 3 seconds). In other words, the frequency of the signal increases from a minimum frequency $f_{min}$ linearly to a maximum frequency $f_{max}$. An ideal signal of this type is plotted in FIG. 23.

In this example, the particle is detected by an appropriate sensor and the resultant signal is recorded, as shown in FIG. 23. As noted, many different systems can be used to accomplish this recording, including those systems described in U.S. Publication No. 2008/0181827.

It should be appreciated that the resultant signal may be generated by virtue of a variety of different patterns and/or associated architectures and/or techniques. However, in at least one form, the overall pattern has a size larger than the particle size. Further, the minimum spacing of the features of the pattern (e.g. the stripes of a pattern) is greater than or equal to the particle size. Patterns of such configuration are advantageous to gain a relatively high spatial resolution, so that information may be had from the resulting signal that will be useful for determining precise locations and positions. In at least one form of the presently described embodiments, determining that a particle is simply within a pattern is insufficient—determining precise locations and positions is an objective. For consistency, to determine a particle position with respect to other particles, or the environment, measurements of time are taken as the particle exits the pattern. Of course, other conventions may be used.

The generalized technique described hereafter has, in at least one form, two basic components: 1) determining the existence and estimated position of a particle and 2) determining particle position to a higher accuracy by applying a correlation technique to the measured signal. It should be understood that exercising the first component of the technique reduces computational effort and, thus, saves system resources.

Figure 24:
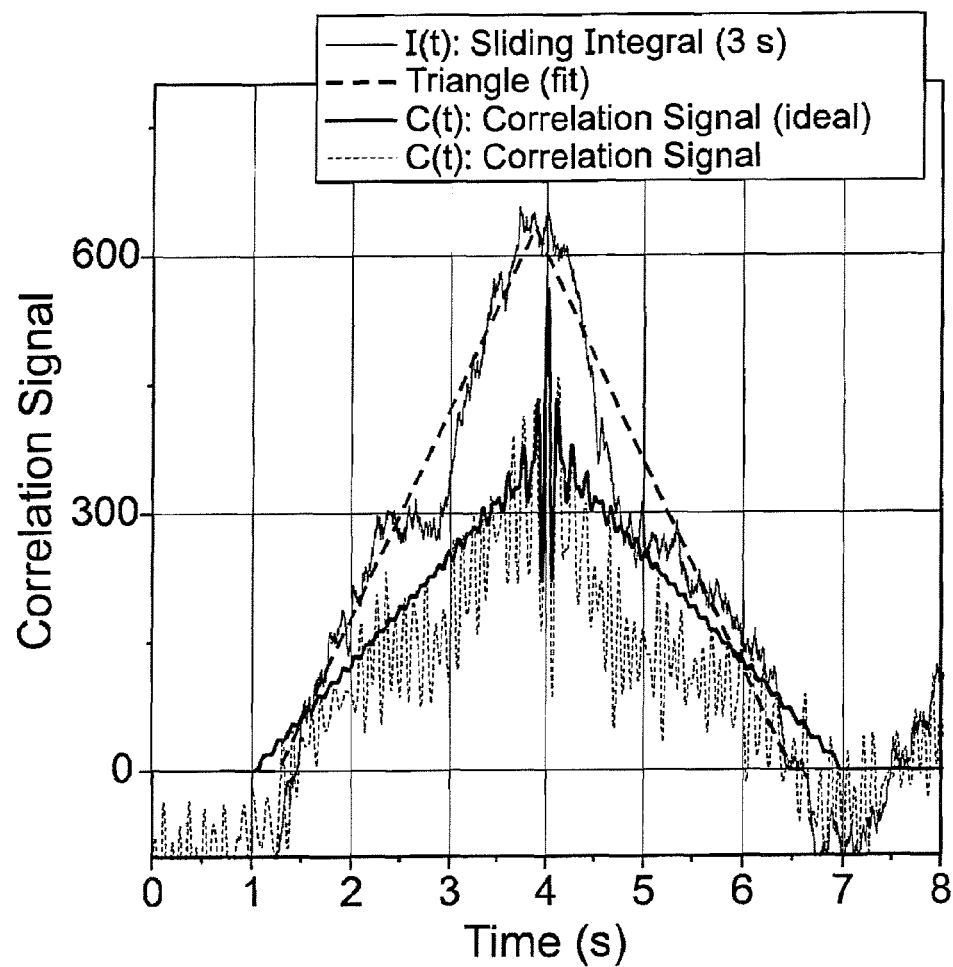
FIG. 24 is a signal used in connection with the presently described embodiments.

With reference now to FIG. 24, a sliding integral is calculated to determine the existence and estimated position of a particle. The sliding integral sums the measured signal S(t) over a defined time period T (e.g. 3 seconds). This calculation is accomplished using the following:

$$I(t) = \int_{t-T}^{t} S(\tau) d\tau$$

Once the sliding integral reaches a predetermined threshold, a particle is detected and the positioning algorithm is triggered. This positioning algorithm includes routines that will fit a triangle to the sliding integral. Fitting the triangle allows for determining a rough estimate of the particle position. To more accurately determine the position, a correlation signal is then calculated using the following:

$$C(t) = \int_{t-T}^{t} S(\tau) P(\tau - t + T) d\tau$$

where,

S(τ) measured signal.

P(τ) is a test signal which is identical to the expected signal which, in this example, is the chirped signal as described above; and T is the length of the chirped test signal P(τ)

Figure 25:
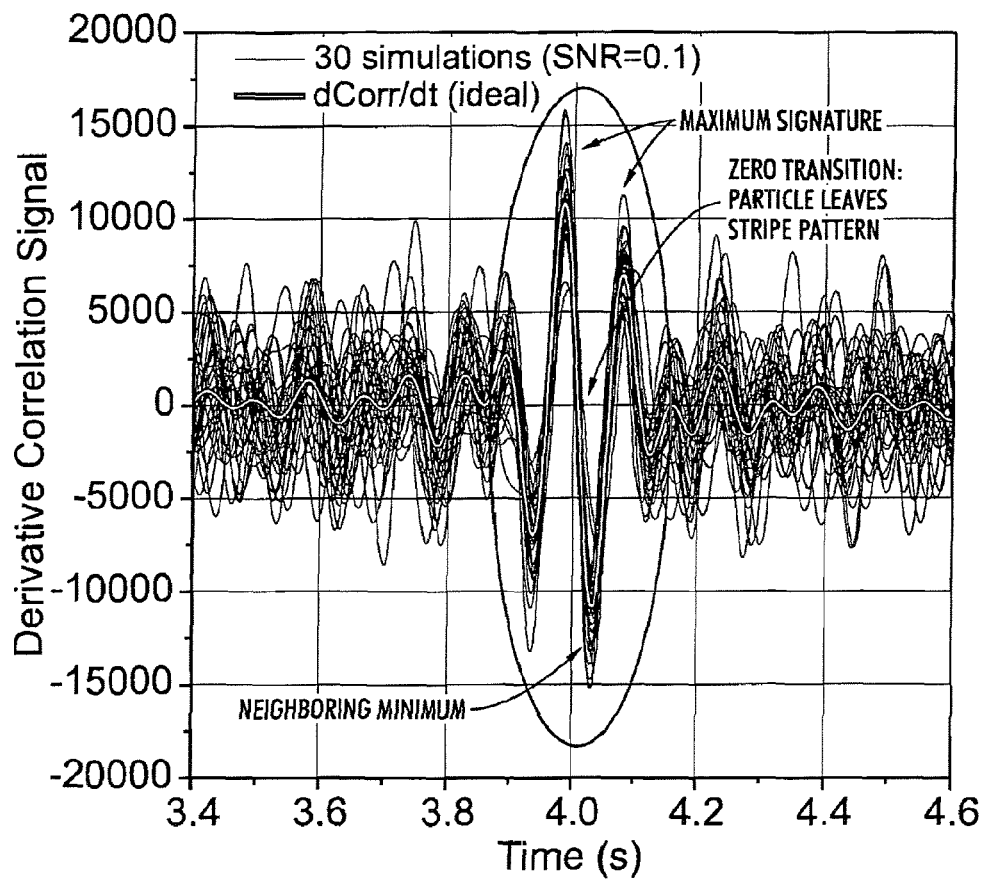
FIG. 25 is a signal used in connection with the presently described embodiments.

FIG. 25 illustrates that the derivative of the correlation signal is then taken. Note that 30 simulations are illustrated as opposed to a single measured and single ideal correlation signal, as in FIG. 24. From the derivative signal, the maximum and minimum in the proximity (e.g. +/−0.5 seconds) of the estimate of the particle position are determined. The maximum difference between the maximum and minimum for all pairs of neighboring maxima and minima is then determined (in this example, one has to compare a maximum and its neighboring minimum to the right). The particle position can then be determined based on the zero transition of the determined maximum difference (zero transition method). In this regard, translation from the zero transition to a position is accomplished as a function of the flow speed of the fluid in the channel. In cases where the fluid is not flowing, the speed of the detector or the microscopic slide, for example, is used to translate the zero transition point to a position.

Figure 26:
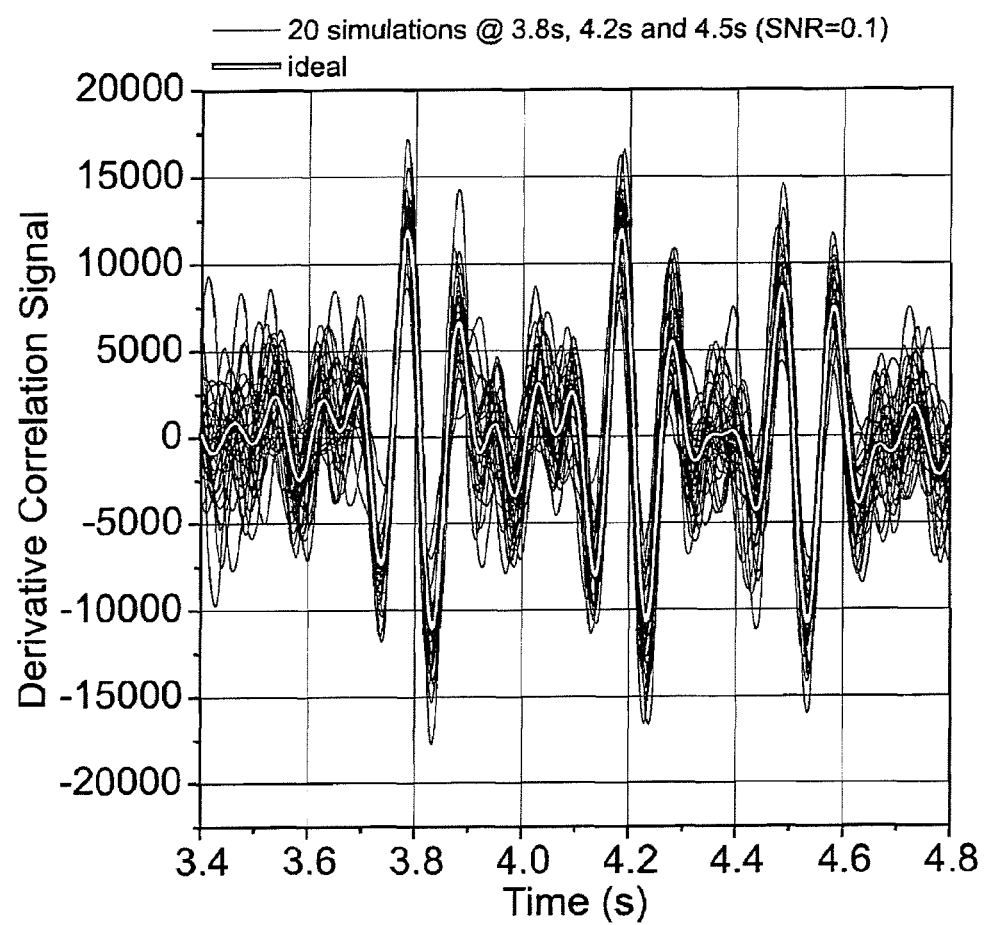
FIG. 26 is a signal used in connection with the presently described embodiments.

The above technique is applied in one form to determine the position of a single particle. However, there is also a need to be able to determine the positions of multiple particles, e.g. two particles. In this case, with reference to FIG. 26, the number of particles within a sliding integral window is evaluated. To do so, the slope of the triangle sides or flanks are measured or the triangle is integrated. The signatures of each particle may be located within the window as described above (zero transition method) in connection with determining the maximum distance between maximums and minimums in the proximity of the estimated position. However, for two particles, the two largest differences (as opposed to only the largest difference) are considered. Again, the signatures are determined relative to the estimated position (e.g. by fitting a calculated ideal signature to the measured signal). Otherwise, the method is the same as above.

Of course, it will be appreciated that this method for determining the position of multiple particles is not effective if the particles are too close together. For the case of the linearly chirped signal in the above mentioned case, a signature width can be defined as (fmax+fmin)/2 fmax fmin, where fmin and fmax are the minimum and maximum frequencies and the frequency of the signal linearly rises from fmin to fmax over the length of the chirped signal. In this regard, if the number of detected particle signatures is smaller than the number of expected particles (as determined by the evaluation techniques above), then it is presumed that at least some of the particles are too close together to be evaluated individually by the zero transition method. Under these circumstances, the ideal correlation signal for two particles is calculated and fitted to the measured correlation signal using particle distance and position of one particle as fit parameter. To obtain reliable fit results, it may be favorable to constrain the parameter particle distance to the signature width.

Figure 27:
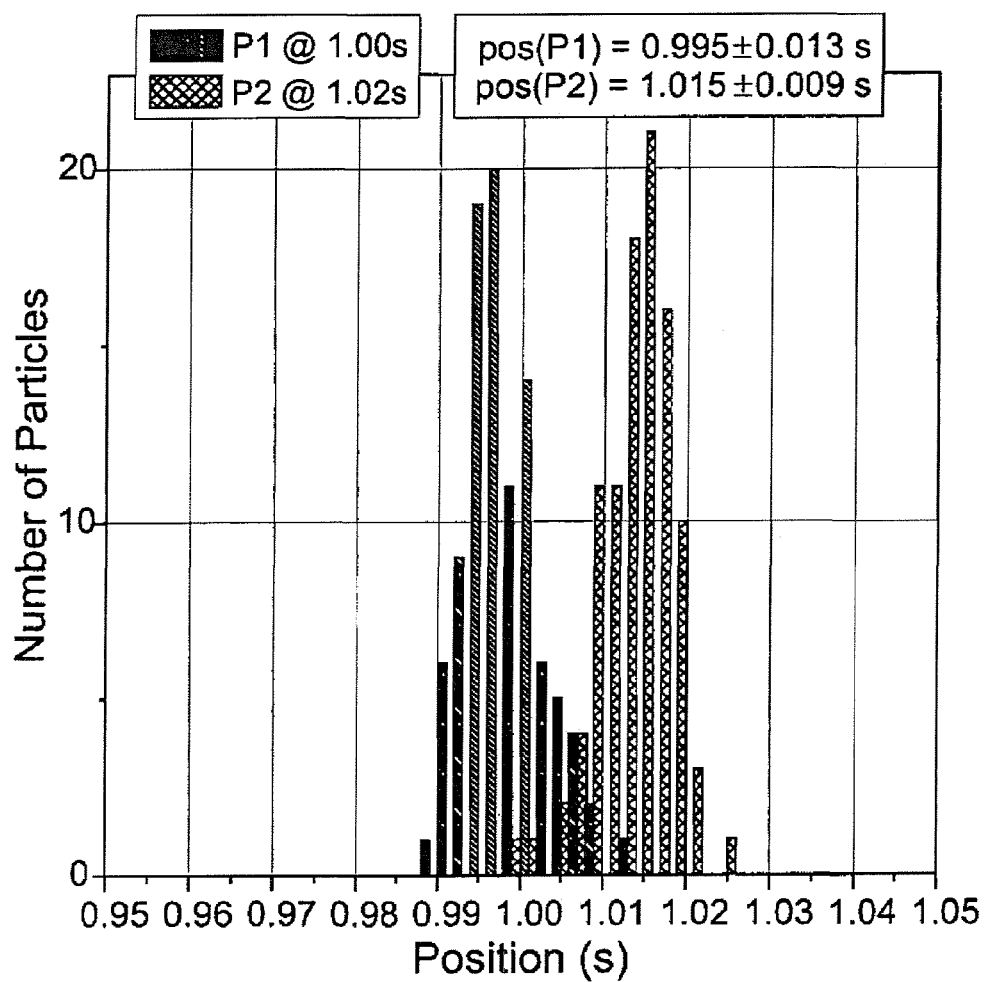
FIG. 27 is a signal used in connection with the presently described embodiments.

With reference now to FIG. 27, simulation results for 100 runs are illustrated. In this simulation, Particle 1 (P1) and Particle 2 (P2) have a distance of 0.02 s where the signature width is 0.11. A low signal to noise ratio of SNR=0.1 is assumed. So, the particles can be distinguished and the position of both particles can be measured by an accuracy of better than ⅕ of the signature width.

Figure 28:
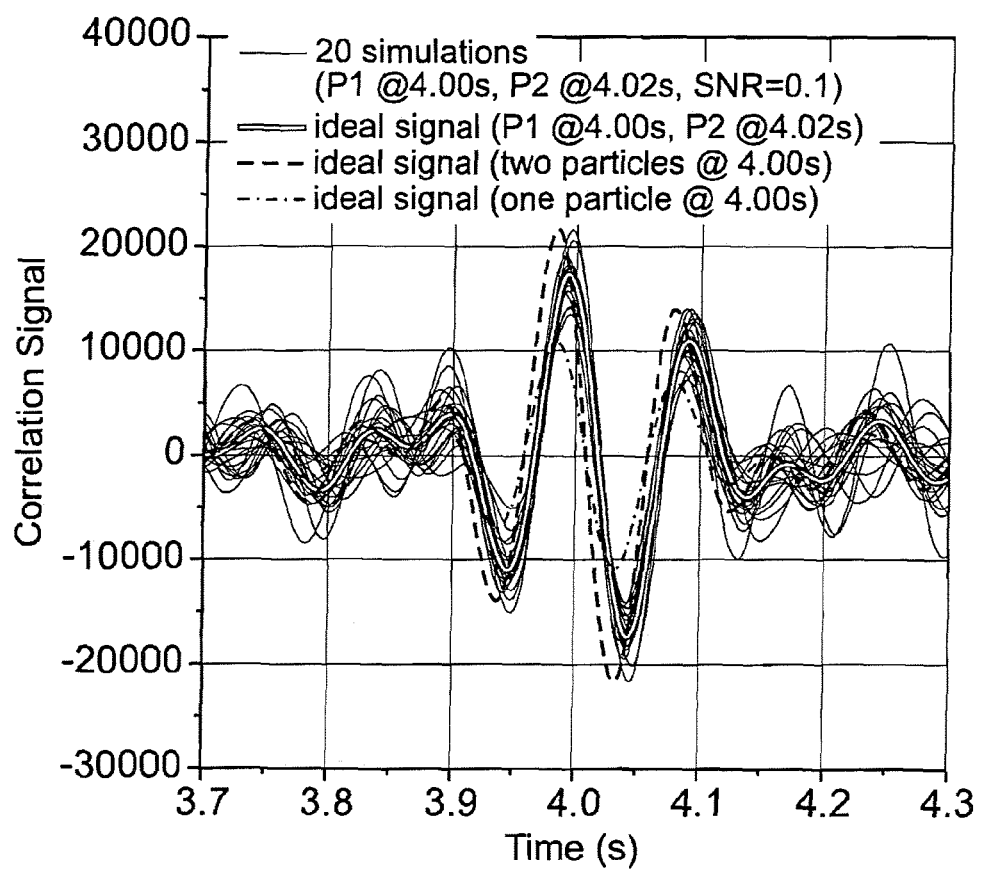
FIG. 28 is a signal used in connection with the presently described embodiments.

Further, referring now to FIG. 28, the overlapping nature of the signature of close particles is illustrated. It can be seen that only one zero transition occurs for the overlapping signal which is composed of the signal of two particles close together. Nevertheless, the particular shape of the overlapping signal is sufficiently different from the case of a single particle and the case of two particles at the same position to be reliably identified. To find the position of each particle, the ideal curve is fitted to the measurement. The parameters of the fit are the positions of each particle.

Further variations of the presently described embodiments are contemplated. As mentioned above, several test functions and fitting functions can be applied.

In addition, in the case of low noise, it might be favorable to skip the correlation enhancement step and fit the signal directly with an appropriate fitting function (e.g., sinusoid).

Fourier-Transformation techniques can be used to determine the frequency and phase of the modulated signals.

The signal processing can either be completely software based as described above or partly done by electronic circuitry. In this regard, it should be understood that the presently described embodiments may be implemented using a variety of different hardware configurations and/or software techniques. The precise implementation may depend on the ultimate application of the presently described embodiments. For example, the presently described embodiments may be implemented as one or a series of software routines that reside on a detector system in a bio-medical system used by a hospital. Or, the routines and techniques of the presently described embodiments may be distributed among a variety of laboratory tools used in an experimental environment. As noted above, in at least one form, the techniques of the presently described embodiments are implemented using a suitable processing module that is capable of processing the data contemplated herein.

The technique can be also applied to data analysis of the fluorescence signal of biochips in order to receive high spatial resolution and high sensitivity.

Moreover, the presently described embodiments have been described in terms of optical or light signals. It will be appreciated that the presently described embodiments may be extended to non-optical signals. For example, capacitance. inductance or resistance could be used to generate a signal to implement the teachings herein.

Figure 13:
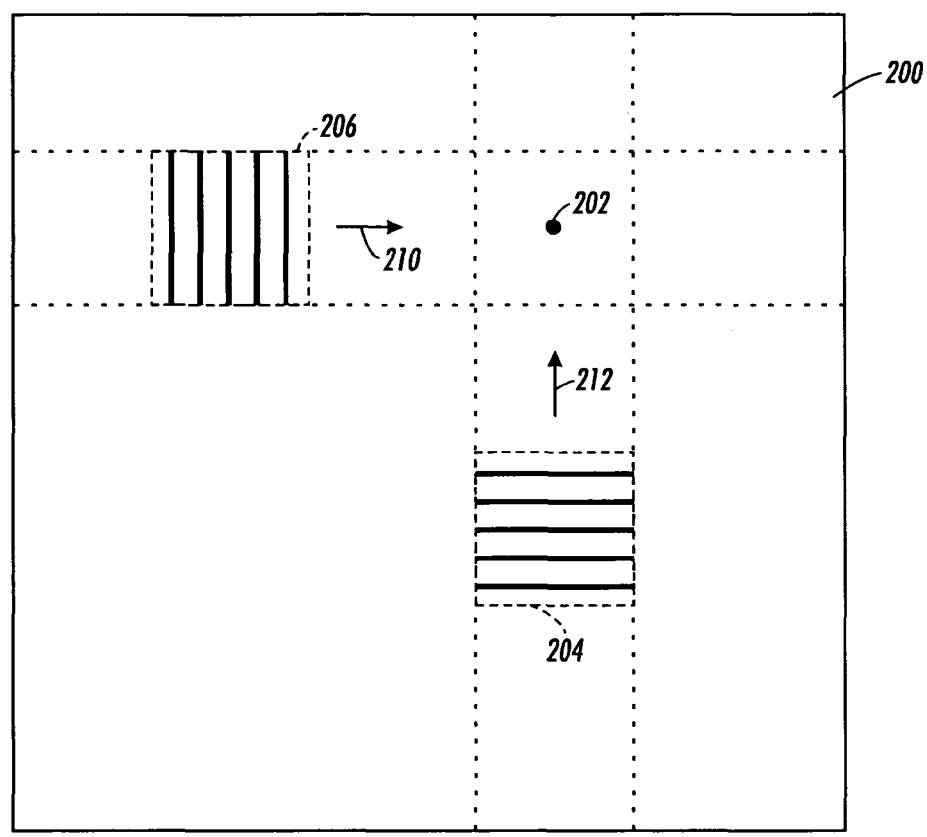
FIG. 13 is a representative view of a presently described embodiment.

More generally, these techniques can be applied to still other kinds of detection for purposes of particle characterization. With reference to FIG. 13, a further embodiment of the presently described embodiments is shown. As note above, the presently described embodiments may be applied not only in one dimension, but in two dimensions as well. In this regard, a particle scanner 200 may be used to locate or localize a particle 202 using a two dimensional technique. The particle 202 may be within a fluid having particles suspended therein and housed on a slide that is positioned on the bed of the scanner 202. The scanner 200 includes a modulation pattern 204 and a modulation pattern 206. The modulation pattern 204 is moved relative to the particle 202 in a first direction 212 while the modulation pattern 206 is subsequently moved relative to the particle 202 in a second direction 210. The first and second directions are, in one form, substantially perpendicular to one another. It should be appreciated that the bed (or a fixture) of the scanner 200 may also be moved to generate the relative motion between the particle and the modulation pattern. It should be further appreciated that the modulation pattern 204 and 206 may be excitation patterns to excite the particle, or optical elements provided to modulate a constant light emission from the particle. The relative movement contemplated will result in detection of light and a corresponding modulated signal that will allow for the determination of the location of the particle. In this regard, the location of the particle may be determined at the position where both modulation patterns yield a suitable signal.

Implementation of such a two dimensional analysis provides advantages. For example, this form of analysis results in a higher spatial resolution. In addition, an improved signal to noise ratio may be experienced.

Further, the presently described embodiments have been described primarily in connection with optical methods of particle characterization, especially those involving visible light. However, it should be appreciated that the presently described techniques and systems may also be applied to other non-optical methods.

Figure 15:
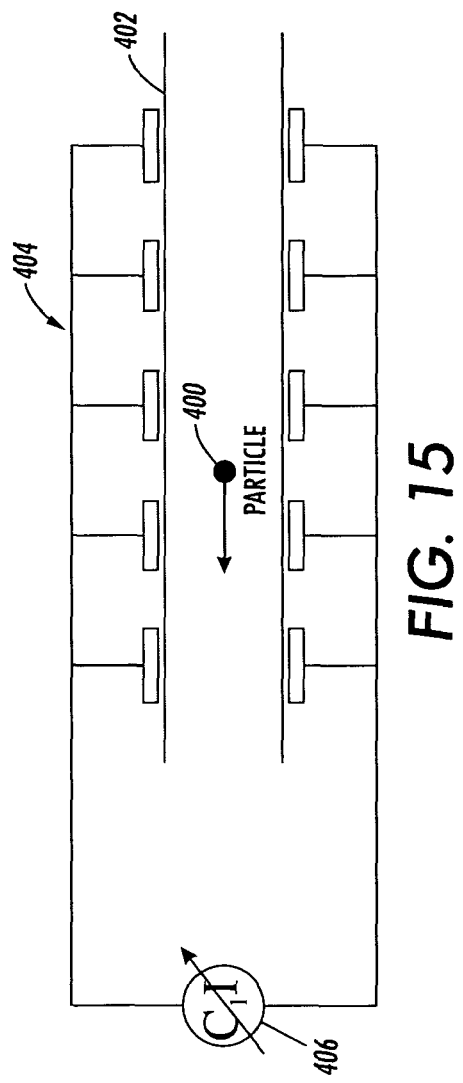

Referring to FIG. 15, an example of a non-optical method is one that utilizes electrical properties (such as capacitance, conductance or impedance) instead of light as a modulated output signal. In this example, a particle 400 may be moved down a channel 402 through an electrode array 404, instead of an optical array. The electrode array 404 is connected to a measurement device 406 and is set up to record the time dependent signal (e.g. capacitance or current) influenced by the moving particle and operates to achieve the objectives of the presently described embodiments described herein.

Figure 14:
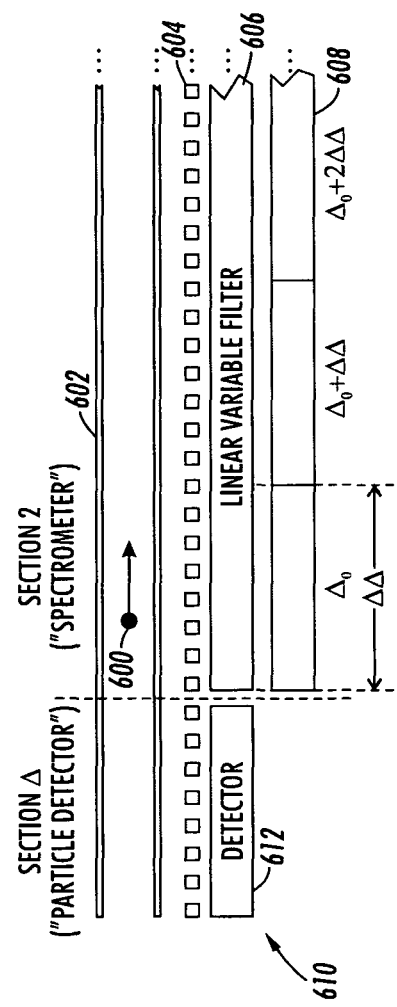
FIG. 14 is a representative view of a presently described embodiment; and,
FIG. 15 is a representative view of a presently described embodiment.

The teachings of the presently described embodiments may be further extended. For example, in all cases where fluorescence intensity is weak and fluorescence particles are moving, this technique can be applied to increase the signal-to-noise ratio. Examples:

Particle/Molecule counting, Cytometry: Counting fluorescent molecules that pass the modulated excitation region with high signal-to-noise ratio Fluorescence spectroscopy: Measuring the fluorescence spectra of particles which pass through the modulated excitation region with high signal-to-noise ratio by coupling the fluorescence light into a spectrometer. With reference to FIG. 14, a particle 600 travels down a channel 602. A shadow mask 604 creates a modulation on each individual pixel of the detector 608. Each pixel of detector 608 records the signal at a particular wavelength over a subrange $\Delta$ determined by the linear variable filter 606. This system may be adjacent a particle detector system 610 having a detector 612.

In accord with the presently described embodiments, relative motion between the particle and the spatially modulated excitation or emission pattern is described. However, instead of moving the particle through the spatially modulated excitation pattern, the detection system can also be scanned along a channel or carrier/chip. In the case of a chip the particles of interest are fixed on the chip and, e.g., the absolute position of particles on the chip is determined.

The concept can, for example, also be applied to fluorescence read-out of a bio-chip.

Spatial modulations can be achieved in different manners. For example, geometry may provide a basis for spatial modulation. In this regard, a spatially modulated shadow mask, e.g. interdigitated finger-type mask, a spatially modulated phase mask, a micro-lens array or a micro-mirror array may be used.

Spatial modulation may also be achieved using electric or magnetic fields. In this regard, emitted fluorescence intensity can be affected by the modulated field. Also, the density of the fluorescence object may be modulated by the field and the optical path can be affected by the field.

Spatially modulated acoustic field (standing or moving acoustic waves, surface acoustic waves) may also be used. In this regard, emitted fluorescence intensity can be impacted by the modulated field. The density of the fluorescence object may be modulated by the field. And, the optical path can be affected by the field.

Spatially modulated environment (e.g. stationary molecular coatings) within the moving path creating a spatially modulated fluorescence quenching may also be useful.

A spatially modulated micro-cavity which influences the emission properties of the moving object may likewise be applied to achieve objectives of the presently described embodiments.

Advantages of the present invention are apparent. First, the location of a particle can be determined with high resolution by analyzing the time dependence of a generated signal. This is enabled by a spatially modulated excitation pattern (e.g., interference pattern) in combination with a relative movement between a particle and excitation pattern.

Second, the lower bound of the spatial resolution is determined by the feature size of an interference pattern which can be chosen much smaller that 1 µm. Dependent upon the signal-to-noise ratio, the time coding of the signal, the relative speed of the particles and the pattern, the sampling rate of the detector, and the applied evaluation technique, it is feasible to achieve a spatial resolution better than the feature size of the interference pattern.

Third, the analyzed signal is modulated with periodic excitation variation. Lock-in techniques or correlation techniques can be applied to significantly enhance the signal-to-noise ratio.

Fourth, no critical optics are needed to focus the excitation light into a very small volume or collect light out of a small volume.

Fifth, the techniques can be integrated into a lab-on-a-chip platform and can be easily extended to parallel multi-fluidic-channel analysis.

Sixth, several fluorescent particles which are within the interference pattern can be detected simultaneously. The feature size of the interference pattern determines the distance between two particles, which can be separated. Dependent upon the signal-to-noise ratio, the time coding of the signal, the relative speed of the particles and the pattern, the sampling rate of the detector, and the applied evaluation technique, it is feasible to achieve a particle separation better than the feature size of the interference pattern.

Seventh, reduced intensity of the excitation light reduces damage, e.g. on living cells or bleaching of dyes.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method of characterizing particles, the method comprising:
creating relative movement between at least one particle and an excitation region;
generating a spatially modulated excitation pattern within the excitation region, the spatially modulated excitation pattern including multiple high excitation areas interspersed with multiple low excitation areas, the spatially modulated excitation pattern extending along a length of the excitation region;
stimulating energy emission from the particle as the particle moves along the length of the excitation region;
detecting the energy emission from the particle using a detector;
generating a detector signal that is time modulated according to the spatially modulated excitation pattern;
analyzing the time modulated detector signal; and
characterizing the particle based on the analysis, wherein generating the spatially modulated excitation pattern within the excitation region comprises generating the spatially modulated excitation pattern based on at least one of an electric field, a magnetic field, and an acoustic standing wave.

2. The method as set forth in claim 1, wherein analyzing the time modulated detector signal comprises at least one of determining a location of the particle based on the signal, counting particles based on the signal, and sorting particles based on the signal.

3. The method as set forth in claim 1, wherein the detecting comprises detecting using a pixilated detector.

4. The method as set forth in claim 1,
wherein the particle is a portion of a DNA molecule or a molecule attached to the DNA molecule and the detector signal is used to determine a DNA sequence.

5. The method as set forth in claim 1, wherein the detecting comprises using a spectrometer to receive a fluorescent spectrum of a fluorescing analyte.

6. The method as set forth in claim 1, wherein generating the spatially modulated excitation pattern comprises generating a spatially modulated pattern based on environment.

7. The method as set forth in claim 1, wherein generating the spatially modulated excitation pattern extending along a length of the excitation region comprises:
generating a first spatially modulated excitation pattern extending along a length of the excitation region in a first direction; and
generating a second spatially modulated excitation pattern extending along a length of the excitation region in a second direction that is substantially orthogonal to the first direction.

8. The method as set forth in claim 1, wherein the energy emitted includes at least one of fluorescence excitation, elastic light scattering, inelastic light scattering, and chemo-luminescence.

9. The method of claim 1,
wherein analyzing the time modulated detector signal includes using a triangular fit function.

10. The method of claim 1, wherein analyzing the time modulated detector signal includes applying a fit function.

11. A method of characterizing particles, the method comprising:
generating a spatially modulated excitation pattern within an excitation region based on at least one of an electric field, a magnetic field, and an acoustic standing wave;
creating relative movement between at least one particle and the excitation region, the particle being excited upon exposure to the spatially modulated excitation pattern within the excitation region, the spatially modulated excitation pattern comprising multiple high excitation regions interspersed with multiple low excitation regions, the spatially modulated excitation pattern stimulating time modulated energy emission from the particle;
detecting the time modulated energy emission from the particle using a detector and generating a time modulated detector signal, the time modulated detector signal being time modulated based on the spatially modulated excitation pattern; and
extracting particle information by
detecting a presence of the particle by calculating an integral of the time modulated signal over a predetermined time period; and
triggering a positioning algorithm after the integral reaches a predetermined threshold, the positioning algorithm including applying a fit function to the time modulated signal.

12. A method comprising:
creating relative movement between at least one particle and an excitation region;
generating a spatially modulated excitation pattern within the excitation region based on a non-optical field, the spatially modulated excitation pattern including multiple high excitation areas interspersed with multiple low excitation areas, the spatially modulated excitation pattern extending along a length of the excitation region;
stimulating energy emission from the particle as the particle moves along the length of the excitation region;
detecting the energy emission from the particle using a detector; and
generating a detector signal that is time modulated according to the spatially modulated excitation pattern.

13. The method of claim 12, wherein the non-optical field is an electric field.

14. The method of claim 12, wherein the non-optical field is a magnetic field.

15. The method of claim 12, wherein the non-optical field is an acoustic standing wave.

16. The method of claim 12, wherein the particle is a portion of a DNA molecule or a molecule attached to the DNA molecule and the detector signal is used to determine a DNA sequence.

17. The method of claim 12, further comprising:
analyzing the time modulated detector signal; and
characterizing the particle based on the analysis.

18. The method of claim 17, wherein analyzing the time modulated detector signal comprises at least one of determining a location of the particle based on the signal, counting particles based on the signal, and sorting particles based on the signal.

19. The method of claim 17, wherein analyzing the time modulated detector signal includes applying a fit function.

20. The method of claim 19, wherein the fit function is a triangular fit function.

21. A method comprising:
creating relative movement between at least one particle and an excitation region;
generating a spatially modulated excitation pattern within the excitation region based on a non-optical field, the spatially modulated excitation pattern including multiple high excitation areas interspersed with multiple low excitation areas, the spatially modulated excitation pattern extending along a length of the excitation region; and
generating a detector signal that is time modulated according to the spatially modulated excitation pattern.

22. The method of claim 21, wherein the spatially modulated excitation pattern comprises electrical properties.

23. The method of claim 21, wherein the detector signal is based on capacitance.

24. The method of claim 21, wherein the detector signal is based on resistance.

25. The method of claim 21, wherein the detector signal is based on inductance.

26. The method of claim 21, wherein the detector signal is a current signal.

27. The method of claim 21, wherein the non-optical field is an electric field.

28. The method of claim 21, further comprising:
analyzing the time modulated detector signal including applying a fit function; and
characterizing the particle based on the analysis.

* * * * *